(12) United States Patent
Jon et al.

(10) Patent No.: US 11,896,681 B2
(45) Date of Patent: Feb. 13, 2024

(54) PARTICLES COMPRISING BILIRUBIN DERIVATIVE AND METAL

(71) Applicant: BILIX CO., LTD., Seoul (KR)

(72) Inventors: Sang Yong Jon, Daejeon (KR); Dong Yun Lee, Daejeon (KR); Yong Hyun Lee, Daejeon (KR); Do Hyun Yoo, Daejeon (KR); Won Sik Jung, Daejeon (KR)

(73) Assignee: BILIX CO., LTD., Seoul (KR)

( * ) Notice: Subject to any disclaimer, the term of this patent is extended or adjusted under 35 U.S.C. 154(b) by 412 days.

(21) Appl. No.: 16/343,043

(22) PCT Filed: May 14, 2018

(86) PCT No.: PCT/KR2018/005515
§ 371 (c)(1),
(2) Date: Apr. 18, 2019

(87) PCT Pub. No.: WO2018/208137
PCT Pub. Date: Nov. 15, 2018

(65) Prior Publication Data
US 2020/0230261 A1    Jul. 23, 2020

(30) Foreign Application Priority Data
May 12, 2017    (KR) .................. 10-2017-0059597

(51) Int. Cl.
| A61K 49/00 | (2006.01) |
| A61K 49/10 | (2006.01) |
| A61K 33/243 | (2019.01) |
| A61K 33/242 | (2019.01) |
| A61K 33/26 | (2006.01) |
| A61K 47/22 | (2006.01) |
| G01N 33/72 | (2006.01) |

(52) U.S. Cl.
CPC .......... *A61K 49/106* (2013.01); *A61K 33/242* (2019.01); *A61K 33/243* (2019.01); *A61K 33/26* (2013.01); *A61K 47/22* (2013.01); *G01N 33/728* (2013.01)

(58) Field of Classification Search
CPC .. A61K 49/106; A61K 33/242; A61K 33/243; A61K 33/26; A61K 47/22; A61K 47/6915; A61K 31/409; A61K 49/0428; A61K 49/186; A61K 51/065; A61K 51/1237; A61K 51/0451; A61K 49/1818; A61K 51/1241; A61K 47/69; A61K 49/04; A61K 49/18; A61K 51/04; A61K 51/06; A61K 51/12; G01N 33/728
See application file for complete search history.

(56) References Cited

U.S. PATENT DOCUMENTS

| 2008/0070971 A1 | 3/2008 | Wang |
| 2012/0305802 A1 | 12/2012 | Herz et al. |
| 2017/0028076 A1 | 2/2017 | Jon et al. |

FOREIGN PATENT DOCUMENTS

| EP | 3088353 A1 | 11/2016 |
| KR | 2015-0079436 A | 7/2015 |
| WO | WO 01/96345 A1 | 12/2001 |
| WO | WO-2017/070676 A1 | 4/2017 |

OTHER PUBLICATIONS

Shukla et al. (J. Nanopart. Res. (2012) 14:981, p. 1-11).*
Lee et al. (Angew. Chem. Int. Ed. 2016, 55, 7460-7463).*
Puranam et al. J. Biosci. Nov. 1987, 485-493.*
Mccullars et al. (Clinica Chimica Acta 1977, 74, 33-38; see abstract).*
Maity, Mritunjoy et al., "Stability and binding interaction of bilirubin on a gold nano-surface: steady state fluorescence and FT-IR investigation", Physical Chemistry Chemical Physics, 2014.
Lee, Dong Yun et al., "Black Pigment Gallstone Inspired Platinum-Chelated Bilirubin Nanoparticles for Combined Photoacoustic Imaging and Photothermal Therapy of Cancers", Angewandte Chemie, Sep. 22, 2017.
International Search Report from corresponding PCT Application No. PCT/KR2018/005515, dated Feb. 8, 2019.
Examination Report For Application No. 201947051181 dated May 27, 2020 from India patent office in a counterpart India patent application.
Office action dated Sep. 22, 2020 from Russia Patent Office in a counterpart Russia Patent Application No. 2019138568/10(076079) (all the cited references are listed in this IDS.) (English translation is also submitted herewith.).
Sahoo, S. K. et al. "Pegylated Zinc Protoporphyrin: A Water-Soluble Heme Oxygenase Inhibitor with Tumor-Targeting Capacity" Bioconjugate Chemistry, vol. 13, pp. 1031-1038, 2002.
Shih-Kai Chou et al. "Via zinc(II) protoporphyrin to the synthesis of poly(ZnPP-MAA-EGDMA) for the imprinting and selective binding of bilirubin" Biomaterials, vol. 30, pp. 1255-1262, 2009.

(Continued)

*Primary Examiner* — Michael G. Hartley
*Assistant Examiner* — Melissa J Perreira
(74) *Attorney, Agent, or Firm* — The PL Law Group, PLLC

(57) ABSTRACT

The present invention provides hydrophilic bilirubin derivative particles containing a metal, a use thereof, and a preparation method therefor. The bilirubin derivative particles of the present invention form coordinate bonds with various metals, and thus can be used in MR diagnosis, CT diagnosis, photo-acoustic diagnosis, PET diagnosis, or optical diagnosis. The bilirubin derivative particles of the present invention can release an anticancer drug encapsulated therein to the outside by the combination with a platinum-based anticancer drug and the degradation by a stimulation of light/reactive oxygen species, and exhibit anti-inflammatory and anticancer activities, and thus the bilirubin derivative particles of the present invention have a concept of theranostics in which the bilirubin derivative particles can be for therapeutic uses as well as diagnostic uses.

11 Claims, 39 Drawing Sheets

(56) References Cited

OTHER PUBLICATIONS

A.S. Timin, E.V.Rumyancev "Sorbenti bilirubina na osnove mezoporistogo kremnezema, modificirovannogo amonigruppami ialbuminom" Himiya I Himicheskaya Tekhnologiya, V.57(7), pp. 87-91, 2014 (English translation of abstract is submitted herewith.).

Rumyantsev E.V., "Bilirubin and its synthetic analogues: solvation, acid-base, coordination properties and thermo-oxidative destruction", The degree of candidate of chemical sciences, Ivanovo, 2006 (English translation of abstract is submitted herewith.).

Office action dated Mar. 8, 2022 from Japan Intellectual Property Office in a counterpart Japanese Patent Application No. 2020-513477 (all the cited references are listed in this IDS.)(English translation is also submitted herewith.).

Shashi P. Shukla et al., "Interaction of bilirubin with Ag and Au ions: green synthesis of bilirubin-stabilized nanoparticles", Journal of Nanoparticle Research, (2012), vol. 14, Article No. 981, doi: 10.1007/s11051-012-0981-7.

\* cited by examiner

PARTICLES COMPRISING BILIRUBIN DERIVATIVE AND METAL

CROSS-REFERENCE TO RELATED APPLICATIONS

This application is a national phase application of PCT Application No. PCT/KR2018/005515, filed on May 14, 2018, which claims priority to Korean Patent Application No. 10-2017-0059597 filed on May 12, 2017. The entire disclosures of the applications identified in this paragraph are incorporated herein by reference.

FIELD

The present invention was made with the support of the Ministry of Science and ICT under Project No. 2018M3A9B5023527, which was conducted in the program entitled "Bio & Medical Technology Development Program" in the project named "Development of Tumor Microenvironment Targeting And Responsive Drug Delivery Platform Technology", by the Korea Advanced Institute of Science and Technology, under management of the National Research Foundation of Korea, from 1 Apr. 2018 to 31 Dec. 2020.

The present invention relates to particles containing a bilirubin derivative and a metal, a use thereof, and a manufacturing method therefor.

BACKGROUND

Naturally occurring building blocks composed of metal-organic coordination complexes have long been the source of scientific inspiration. For example, the coordination of specific metals and organic ligands plays a key role in the performance of biological functions, such as metalloproteins, photosynthesis (Mg(II)-porphyrin), and oxygen transport (Cu(II)-heme) and attachment (Fe(III)-phenolics). These metal-organic complexes show the potential in not only biomedical fields but also chemical fields including sensors, separation processes, and catalytic actions. However, the application thereof has been very restricted due to toxicity problems and time-consuming manufacturing steps.

Bilirubin, which is the final metabolite of heme metabolism in our body, is a naturally occurring metal-organic coordination material. The present inventors were inspired by gallstone formation, which is a pathological phenomenon occurring in the biliary drainage route, in the strategy of the present invention to use bilirubin as a metal-organic coordination material. Gallstones are calculi formed in the biliary duct by the combination of bile acid with metals due to the abnormal bile metabolism. Bilirubin is excreted into bile acid, and black pigmented gallstones of the gallstones are known as final products of the complexes composed of bilirubin and cupper and/or bilirubin and calcium in the bile acid. Bilirubin is rich in functional groups inherently having unpaired electrons or nonbonding electron pairs, and thus can react with cationic metal ions even without external linkers to thereby form metal-organic coordination complexes. However, bilirubin does not dissolve well in a solvent since it is very hydrophobic, and thus bilirubin is not easy to use chemically.

In order to solve the problem of bilirubin application due to hydrophobicity of the bilirubin and apply bilirubin to various uses, the present inventors developed bilirubin nanoparticles composed of a complex of bilirubin and a hydrophilic polymer, and these bilirubin nanoparticles have been registered as Korean Patent No. 10-1681299, the entire contents of which are incorporated herein by reference.

Throughout the specification, many papers and patent documents are used as references, and the citations thereof are represented. The disclosure of the cited papers and patent documents is incorporated in the present specification by reference in its entirety, to describe a level of a technical field to which the present invention pertains and content of the present invention more clearly.

SUMMARY

Technical Problem

An aspect of the present invention is to provide a bilirubin derivative particle containing a bilirubin derivative and a metal.

Another aspect of the present invention is to provide a contrast agent for image diagnosis, the contrast agent containing the bilirubin derivative particles.

Still another aspect of the present invention is to provide a pharmaceutical composition for treatment and diagnosis of cancer, the composition containing the bilirubin derivative particles.

Still another aspect of the present invention is to provide a pharmaceutical composition for treatment and diagnosis of an inflammatory disease, the composition containing the bilirubin derivative particles.

Still another aspect of the present invention is to provide a method for preparing the bilirubin derivative particle.

Still another aspect of the present invention is to provide a composition for detection of reactive oxygen species (ROS), the composition containing the bilirubin derivative particles.

Still another aspect of the present invention is to provide a sensor for detection of reactive oxygen species (ROS), the sensor including the bilirubin derivative particles.

Still another aspect of the present invention is to provide a method for detection of reactive oxygen species (ROS) by using the bilirubin derivative particles.

Other purposes and advantages of the present disclosure will become more obvious with the following detailed description of the invention, claims, and drawings.

Technical Solution

The present invention provides inventions 1 to 17 below:
1. A bilirubin derivative particle including a bilirubin derivative and a metal.
2. The bilirubin derivative particle of invention 1, wherein the bilirubin derivative particle is configured through a coordinate bond of the bilirubin derivative and the metal.
3. The bilirubin derivative particle of invention 1, wherein the coordinate bond is formed between the metal and a carboxyl group, a lactam group, or a pyrrole ring of the bilirubin derivative.
4. The bilirubin derivative particle of any one of inventions 1 to 3, wherein the metal is an ion or compound of a metal selected from the group consisting of Cu, Ga, Rb, Zr, Y, Tc, In, Ti, Gd, Mn, Fe, Au, Pt, Pd, Ag, Co, Mn, Zn, Gd, Mo, Ni, Fe, Cr, Na, K, Rb, Cs, Mg, Ca, Sr, Ba, Ra, and lanthanide metals.
5. The bilirubin derivative particle of any one of inventions 1 to 3, wherein the metal is a superparamagnetic iron oxide nanoparticle (SPION) or a gold nanoparticle.
6. The bilirubin derivative particle of invention 5, wherein the bilirubin derivative particle is configured in the form in which the metal is located at the center and the bilirubin derivative surrounds the metal.

7. The bilirubin derivative particle of invention 6, wherein the metal is in the form of a single metal particle or clustered metal particles.

8. The bilirubin derivative particle of any one of inventions 1 to 3, wherein the metal is a platinum (Pt) ion or a platinum-based anticancer drug selected from the group consisting of cisplatin, carboplatin, oxaliplatin, nedaplatin, and heptaplatin.

9. The bilirubin derivative particle of any one of inventions 1 to 3, wherein the metal is a radioactive isotope selected from the group consisting of 64Cu, 68Ga, 82Rb, 89Zr, 90Y, 99mTc, 111In, and 201TI.

10. The bilirubin derivative particle of any one of inventions 1 to 9, wherein the bilirubin derivative is a derive in which a hydrophilic molecule is conjugated to bilirubin.

11. The bilirubin derivative particle of invention 10, wherein the hydrophilic molecule is selected from the group consisting of dextran, carbodextran, polysaccharide, cyclodextran, pluronic, cellulose, starch, glycogen, carbohydrate, monosaccharide, bisaccharide and oligosaccharide, polyphosphagen, polylactide, poly(lactic-co-glycolic acid), polycaprolactone, polyanhydride, polymaleic acid and polymaleic acid derivatives, polyalkylcyanoacrylate, polyhydroxybutylate, polycarbonate, polyorthoester, polyethyleneglycol, polypropyleneglycol, polyethylenimine, poly-L-lysine, polyglycolide, polymetacrylate, polyvinylpyrrolidone, poly[acrylate], poly[acrylamide], poly[vinylester], poly[vinyl alcohol], polystryene, polyoxide, polyelectrolyte, poly[1-nitropropylene], poly[N-vinyl pyrrolidone], poly[vinyl amine], poly[beta-hydroxyethylmethacrylate], polyethyleneoxide, poly[ethylene oxide-bpropyleneoxide], polylysine, and peptide.

12. The bilirubin derivative particle of invention 11, wherein the hydrophilic molecule is polyethylene glycol (PET).

13. The bilirubin derivative particle of invention 12, wherein the PEG is selected from the group consisting of methoxy polyethylene glycol (PEG), succinimide of PEG propionic acid, succinimide of PEG butanoic acid, branched PEG-NHS, PEG succinimidyl succinate, succinimide of carboxymethylated PEG, benzotriazole carbonate of PEG, PEG-glycidyl ether, PEG-oxycarbonylimidazole, PEG nitrophenyl carbonates, PEG-aldehyde, PEG succinimidyl carboxymethyl ester, and PEG succinimidyl ester.

14. The bilirubin derivative particle of invention 12, wherein the average molecular weight of the PEG is 200-20000 Da.

15. A composition containing the bilirubin derivative particles of any one of claims 1 to 14.

16. The composition of invention 15, wherein the composition is a contrast agent composition for image diagnosis.

17. The composition of invention 16, wherein the contrast agent composition for image diagnosis is for magnetic resonance (MR) diagnosis, computed tomography (CT) diagnosis, positron emission tomography (PET) diagnosis, or optical diagnosis.

18. The composition of invention 15, wherein the composition is a pharmaceutical composition for treatment of cancer.

19. The composition of invention 18, wherein the cancer is selected from the group consisting of gastric cancer, lung cancer, breast cancer, ovarian cancer, liver cancer, bronchial cancer, nasopharyngeal cancer, laryngeal cancer, pancreatic cancer, bladder cancer, colon cancer, rectal cancer, and cervical cancer.

20. The composition of invention 15, wherein the composition is a pharmaceutical composition for treatment and diagnosis of an inflammatory disease.

21. A method for preparing a bilirubin derivative particle including a metal and a bilirubin derivative, the method including the steps of:
(a) conjugating bilirubin to a hydrophilic molecule to prepare a bilirubin derivative; and
(b) coordinating the bilirubin derivative and a metal to prepare a bilirubin derivative particle having the metal encapsulated therein.

22. The method of invention 21, wherein step (b) includes the following steps:
(b-1) preparing a particle composed of the bilirubin derivative; and
(b-2) encapsulating the metal in the particle composed of the bilirubin derivative.

23. The method of invention 21, wherein in step (b), the preparation of the particle composed of the bilirubin derivative and the encapsulation of the metal are conducted at the same time.

24. The method of invention 15, wherein the composition is for detection of reactive oxygen species (ROS).

25. The method of invention 24, wherein the composition is a contrast agent composition.

26. The method of invention 24, wherein the reactive oxygen species is selected from the group consisting of superoxide ($O^{2-}$), hydrogen peroxide ($H_2O_2$), hydroxy radical (OH), singlet oxygen ($^1O_2$), an organic hydroperoxide (ROOH), alkoxy radical (RO.), peroxy radical (ROO.), or ozone ($O_3$), and nitrogen dioxide ($NO^2$).

27. A sensor for detection of reactive oxygen species (ROS), the sensor including the bilirubin derivative particles of any one of inventions 1 to 14.

28. A method for detection of reactive oxygen species, the method including the steps of:
(a) contacting a suspension containing the bilirubin derivative particles of any one of inventions 1 to 13 with a sample containing reactive oxygen species; and
(b) comparing and analyzing a change of the suspension before and after the contact with the sample with a control group.

29. The method of invention 28, wherein the change of the suspension in step (b) is selected from the group consisting of the presence or absence of precipitation of bilirubin derivative particles, the absorbance according to wavelength, the transparency of the suspension, the concentration of metal ions in the suspension, and the intensity of MRI image signal.

30. A method for image diagnosis, the method including a step of administering, to a subject, a composition containing the bilirubin derivative particles of any one of inventions 1 to 14.

31. A method for treatment of cancer, the method including a step of administering, to a subject, a composition containing the bilirubin derivative particles of any one of inventions 1 to 14.

32. A method for treatment and diagnosis of an inflammatory disease, the method including a step of administering, to a subject, a composition containing the bilirubin derivative particles of any one of inventions 1 to 14.

In accordance with an aspect of the present invention, there is provided a bilirubin derivative particle containing a bilirubin derivative and a metal.

The present inventors were inspired by gallstones, which are complexes formed between cupper (Cu) and bilirubin as an organic ligand in the human body, and endeavored to develop nanoparticles capable of utilizing coordinate bonding characteristics of bilirubin to various uses. As a result, the present inventors prepared: water-soluble bilirubin derivatives formed by introducing hydrophilic molecules into bilirubin; and bilirubin derivative particles formed by self-assembly of the bilirubin derivative, and confirmed chelating effects thereof with respect to various metals and the applicability thereof as contrast agents for image diagnosis and therapeutic agents for inflammation diseases and cancer diseases.

According to an embodiment of the present invention, the bilirubin derivative particle of the present invention forms a metal complex through a coordinate bond with the metal.

The metal complex of the present invention refers to a single atomic body formed by three-dimensional coordination of several other ion molecules or atomic groups with directivity centering on at least one metal atom or ion. Here, the ion molecules or atomic groups coordinated to the metal atom or ion as a center is called ligands. In the bilirubin derivative particle of the present invention, the bilirubin derivative is a ligand and the metal bonding with the bilirubin derivative is a central metal.

According to an embodiment, the coordinate bond is formed between a metal ion and a carboxyl group, a pyrrole ring, or a lactam group of the bilirubin derivative.

The sites in the bilirubin molecule, at which the coordinate bond can be formed, are indicated by dotted circles in Chemical Formula 1 below.

[Chemical Formula 1]

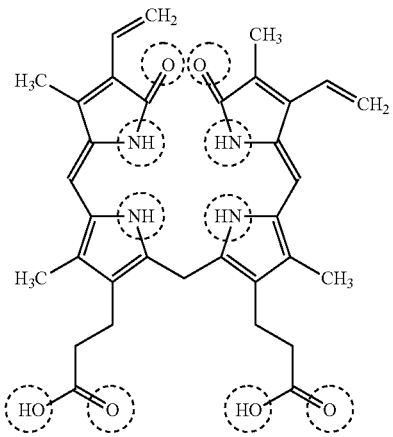

According to an embodiment, the metal contained by binding with the bilirubin derivative of the present invention through a coordinate bond may be an ion or compound of a metal selected from the group consisting of Cu, Ga, Rb, Zr, Y, Tc, In, Ti, Gd, Mn, Fe, Au, Pt, Pd, Ag, Co, Mn, Zn, Gd, Mo, Ni, Fe, Cr, Na, K, Rb, Cs, Mg, Ca, Sr, Ba, Ra, and lanthanide metals, but is not limited thereto.

According to a specific embodiment of the present invention, the bilirubin derivative of the present invention binds with various metal particles including a superparamagnetic iron oxide nanoparticle (SPION) and a gold nanoparticle AuNP.

As confirmed in an example below, the bilirubin derivative of the present invention bound with a superparamagnetic iron oxide nanoparticle (SPION) to form a nanoparticle (FIGS. 6a to 6c), and such SPION-bound bilirubin derivative particles showed excellent relaxivity compared with an existing clinically used T2-weighted MR contrast agent, Feridex, and thus can be favorably used as a contrast agent for MRI contrast enhancement (FIG. 7).

According to an embodiment of the present invention, the bilirubin derivative particles of the present invention can scavenge reactive oxygen species. As confirmed in an example below, the bilirubin derivative particle containing SPION of the present invention aggregated in response to the treatment with hypochlorite as reactive oxygen species (ROS) generator (FIG. 8), and thus can be used to treat inflammation by scavenging reactive oxygen species in the inflammation tissue.

Therefore, the bilirubin derivative particles of the present invention can also be favorably used as a pharmaceutical composition for treatment of an inflammation disease.

In addition, the bilirubin derivative particles of the present invention can also be favorably used as a pharmaceutical composition for treatment of a cancer disease or an angiogenic disease because of an anticancer action and an angiogenic inhibitory action of the bilirubin derivative particles per se, as disclosed in Korean Patent No. 10-1681299.

According to an embodiment of the present invention, the bilirubin derivative particle is formed in the form in which the metal is located at the center and the bilirubin derivative surrounds the metal.

According to a specific embodiment of the present invention, the bilirubin derivative particle containing a metal of the present invention may be prepared in two distinctive particle forms: a form of clustered metal particles in which several metal particles form a cluster; and a form of uniform metal particles in which respective metal particles are uniformly distributed.

As confirmed in an example below, the present inventors applied two methods to configure PEG-bilirubin coated iron oxide nanoparticles, in order to investigate whether the bilirubin derivative particles of the present invention could be prepared in the two forms. As a result, the present inventors confirmed from TEM images that two types of particles were successfully prepared using PEG-bilirubin shells (FIG. 6c).

According to a specific embodiment of the present invention, the metal included in the bilirubin derivative particle of the present invention is a platinum-based anticancer drug selected from the group consisting of cisplatin, carboplatin, oxaliplatin, nedaplatin, and heptaplatin. As confirmed in an example below, the bilirubin derivative particles of the present invention can effectively load cisplatin (FIG. 15). The expected binding form between the cisplatin and the bilirubin derivative particle of the present invention is shown in FIG. 16.

According to a specific embodiment of the present invention, the bilirubin derivative particle containing a platinum-based anticancer drug of the present invention can release the loaded anticancer drug to the surrounding by a stimulation of light, reactive oxygen species, or acidic pH (FIGS. 17a and 17b).

Therefore, the bilirubin derivative particles of the present invention can be used as an active ingredient for cancer treatment due to the foregoing anticancer actions/angiogenic inhibitory actions of the bilirubin derivative itself as well as platinum-based anticancer drug loading and release characteristics of the bilirubin derivative.

As used herein, the term "bilirubin derivative" refers to a hydrophilic or amphiphilic compound formed by the conjugation of bilirubin with a hydrophilic molecule. The bilirubin derivative of the present invention forms a coordinate bond together with a metal component to prepare the bilirubin derivative particle of the present invention.

According to an embodiment of the present invention, the hydrophilic molecule is conjugated to a carboxyl group of bilirubin to form a hydrophilic or amphiphilic bilirubin derivative (see Amphiphiles: Molecular Assembly and Applications (ACS Symposium Series) 1st Edition by Ramanathan Nagarajan and Various Self-Assembly Behaviors of Amphiphilic Molecules in Ionic Liquids By Bin Dong and Yanan Gao, DOI:10.5772/59095). The carboxyl group of bilirubin is conjugated to an amine group of the hydrophilic molecule through amine conjugation (ex. EDC/NHS reaction) or a hydroxyl group of the hydrophilic molecule through esterfication reaction (see Conjugated Chitosan as a Novel Platform for Oral Delivery of Paclitaxel, Lee et al., J. Med. Chem., 2008, 51 (20), p. 6442-6449, DOI: 10.1021/jm800767c). Bilirubin in the form of having a hydrophilic molecule conjugated thereto has an amphiphilic property to be soluble in an aqueous solvent, and thus is useful for chemical handling, and such bilirubin spontaneously self-assembles to form a particle, and thus can be applied to both hydrophobic and hydrophilic preparations. In an example of the present invention, the present inventors prepared PEGylated bilirubin (PEG-BR, PEG-bilirubin) as a bilirubin derivative according to the present invention through a simple reaction in which an amide bond is formed on a carboxylic acid salt by using polyethylene glycol (PEG) as a hydrophilic compound.

Examples of the hydrophilic molecule usable in the present invention may include dextran, carbodextran, polysaccharide, cyclodextran, pluronic, cellulose, starch, glycogen, carbohydrate, monosaccharide, bisaccharide and oligosaccharide, polyphosphagen, polylactide, poly(lactic-co-glycolic acid), polycaprolactone, polyanhydride, polymaleic acid and polymaleic acid derivatives, polyalkylcyanoacrylate, polyhydroxybutylate, polycarbonate, polyorthoester, polyethyleneglycol, polypropyleneglycol, polyethylenimine, poly-L-lysine, polyglycolide, polymetacrylate, polyvinylpyrrolidone, poly[acrylate], poly[acrylamide], poly[vinylester], poly[vinyl alcohol], polystryene, polyoxide, polyelectrolyte, poly[1-nitropropylene], poly[N-vinyl pyrrolidone], poly[vinyl amine], poly[beta-hydroxyethylmethacrylate], polyethyleneoxide, poly[ethylene oxide-bpropyleneoxide], polylysine, and peptide.

According to an embodiment of the present invention, the hydrophilic polymer is polyethylene glycol or a derivative thereof. Examples of the polyethylene glycol derivative may include methoxy polyethylene glycol (PEG), succinimide of PEG propionic acid, succinimide of PEG butanoic acid, branched PEG-NHS, PEG succinimidyl succinate, succinimide of carboxymethylated PEG, benzotriazole carbonate of PEG, PEG-glycidyl ether, PEG-oxycarbonylimidazole, PEG nitrophenyl carbonates, PEG-aldehyde, PEG succinimidyl carboxymethyl ester, and PEG succinimidyl ester (see PEGylated polymers for medicine: from conjugation to self-assembled systems, Jorlemon et al., Chem. Commun., 2010, 46, 1377-1393).

According to a specific embodiment of the present invention, the average molecule weight of the polyethylene glycol is 200-20000 Da.

Still another example of the hydrophilic polymer usable in the present invention may include a peptide composed of two or more (e.g., 2-50) amino acids. The amino acids may include natural amino acids and non-natural amino acids. The hydrophilic amino acids include glutamine, aspartic acid, glutamic acid, threonine, asparagine, arginine, and serine, and the hydrophobic amino acids include phenylalanine, tryptophan, isoleucine, leucine, proline, methionine, valine and alanine. Examples of the non-coded hydrophilic amino acid may include Cit and hCys. A person skilled in the art could easily synthesize the hydrophilic peptides on the basis of such information and peptide synthesis techniques to use the hydrophilic peptides in the manufacturing of and bilirubin nanoparticles.

The hydrophilic polymer includes not only the above-mentioned polymers but also derivatives thereof. More specifically, the hydrophilic molecules may have an amine group or a hydroxyl group or may be modified to have an amine group or a hydroxyl group. It would be obvious to a person skilled in the art that the carboxyl group of bilirubin of the present invention can be conjugated very easily to an amine group of the hydrophilic molecules through an amide group or to a hydroxyl group through an esterfication reaction.

In accordance with another aspect of the present invention, there is provided a contrast agent for image diagnosis, the contrast agent containing the bilirubin derivative particle containing a metal.

According to an embodiment of the present invention, the contrast agent for image diagnosis may be used for magnetic resonance (MR) diagnosis, computed tomography (CT) diagnosis, positron emission tomography (PET) diagnosis, or optical diagnosis.

The use for optical diagnosis of the present invention includes photo-acoustic diagnosis and a diagnosis method (use) using a fluorescent image. The photo-acoustic diagnosis has been validated through an example of the present invention by binding a cisplatin metal to a bilirubin derivative. For the fluorescent image, fluorescence characteristics of lanthanide metals, such as Eu (III) and Tb (III), are used. The fluorescent wavelength bands or intensities thereof of the lanthanide metals are controlled by binding a bilirubin derivative to the lanthanide metals, so that imaging is possible by detecting the fluorescence released by the lanthanide metals.

Specifically, the bilirubin derivative particles of the present invention may be applied to nuclear medicine imaging ($^{64}$C, $^{68}$Ga, $^{82}$Rb, $^{89}$Zr, $^{90}$Y, $^{99}$mTc, $^{111}$In, and $^{201}$Tl), MR imaging (Gd, Mn, and Fe), and CT imaging (Au) by introducing various metal ions into the bilirubin derivatives without external linkers. Especially, in the conventional contrast agents used in magnetic resonance imaging or computed tomography, ligands were manipulated by providing external linkers and metals to complexes, but the bilirubin derivatives of the present invention can bind to the metals quickly and effectively without separate linkers.

In an accordance with still another aspect of the present invention, there is provided a pharmaceutical composition for treatment and diagnosis of cancer, the composition containing the bilirubin derivative particles containing a metal.

According to an embodiment of the present invention, the cancer may be gastric cancer, lung cancer, breast cancer, ovarian cancer, liver cancer, bronchial cancer, nasopharyngeal cancer, laryngeal cancer, pancreatic cancer, bladder cancer, colon cancer, rectal cancer, and cervical cancer.

The bilirubin derivative particles of the present invention exhibit anti-angiogenic activity, and thus can be used in the prevention and treatment of cancer. Specifically, when the bilirubin derivative particles loading a platinum-based anticancer drug, such as cisplatin, are administered into the body, the bilirubin derivative particles are accumulated in the tumor tissue by an EPR effect. Here, when an external light is irradiated to the tumor tissue, a hydrophobic layer made of bilirubin is transformed into a hydrophilic layer containing a hydrophilic photoisomer, resulting in nanoparticle disassembly (breakdown), and thus the anticancer drug contained in the nanoparticles is released to the tumor tissue, leading to cancer treatment. At the same time, the monomers degraded from the nanoparticles bind with albumin, and thus fluorescence is released from the tumor tissue, thereby allowing the imaging of the tumor tissue using the fluorescence.

As confirmed in an example below, the bilirubin derivatives of the present invention effectively formed coordination complexes together with $^{64}Cu$, superparamagnetic iron oxide nanoparticle (SPION), gold nanoparticle (GNP), an ion of a metal, such as Ni, Mn, Gd, Mg, Ca, and Fe, and a platinum-based anticancer drug, and thus the bilirubin derivatives can attain chelation with various metals and can be applied for various uses (FIGS. 5a and 5b).

Meanwhile, the bilirubin derivative particles of the present invention are selectively accumulated in tumor tissues and produce a photothermal effect of generating high heat when irradiated with a predetermined wavelength of light, and thus can be used in the treatment of cancer diseases.

As shown in an example below, the present inventors first applied cisplatin-bilirubin derivative particles to in vivo photo-acoustic imaging in tumor xenograft model mice, and as a result, it was confirmed that the photo-acoustic signal was gradually increased after intravenous injection (FIG. 18) and the surface temperature of the tumor was rapidly increased to 55-60° C. within 5 minutes after the exposure to light of 808 nm, so that the bilirubin derivative particles of the present invention can be utilized in photo-acoustic imaging as well as photo-thermal therapy (PTT) (FIG. 19).

In accordance with still another aspect of the present invention, there is provided a pharmaceutical composition for treatment and diagnosis of an inflammatory disease, the composition containing the bilirubin derivative particles containing a metal.

The bilirubin nanoparticles of the present invention may be utilized as an ROS-sensitive material for diagnosis and treatment of an inflammatory diseases. Specifically, the bilirubin derivative particles, which are parenterally administered into the body, can target an inflammatory site by an EPR effect.

In addition, the bilirubin derivative particles can scavenge an abnormal level of reactive oxygen species in an inflammation site, to thereby exhibit anti-inflammatory activity, and thus can treat inflammation.

Examples of the inflammatory disease, to which the present invention can be applied, may include inflammatory bowel disease, atopic dermatitis, edema, dermatitis, allergies, asthma, conjunctivitis, periodontitis, rhinitis, otitis media, atherosclerosis, pharyngolaryngitis, tonsillitis, pneumonia, gastric ulcers, gastritis, Crohn's disease, colitis, hemorrhoids, gout, ankylosing spondylitis, rheumatic fever, lupus, fibromyalgia, psoriatic arthritis, osteoarthritis, rheumatoid arthritis, Periarthritis of shoulder, tendinitis, tenosynovitis, myositis, hepatitis, cystitis, nephritis, Sjogren's syndrome, and multiple sclerosis, but are not limited thereto.

According to an embodiment of the present invention, the bilirubin derivative particle of the present invention can be coordinated to a metal ion. The metal ion-coordinated bilirubin derivative particle of the present invention reacts with reactive oxygen species, such as hypochlorite, resulting in particle breakdown, thereby releasing the metal ion. According to a specific embodiment of the present invention, the manganese ion ($Mg^{2+}$)-coordinated bilirubin derivative particle reacts with reactive oxygen species, such as hypochlorite, thereby rereleasing manganese ions. Therefore, a change in T1 value in the magnetic resonance image of the manganese ion between when the manganese ion is coordinated by a bilirubin derivative and when the manganese ion is released results in a change in brightness of the MRI images, thereby detecting reactive oxygen species.

The composition of the present invention, when being a pharmaceutical composition, contains a pharmaceutically acceptable carrier. The pharmaceutically acceptable carrier is abnormally used at the time of formulation, and examples thereof may include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methylcellulose, methyl hydroxybenzoate, propyl hydroxybenzoate, talc, magnesium stearate, and mineral oil. The pharmaceutical composition of the present invention may further contain a lubricant, a wetting agent, a sweetening agent, a flavoring agent, an emulsifier, a suspending agent, a preservative, and the like, in addition to the above ingredients.

The pharmaceutical composition of the present invention can be used through parenteral administration, which may be, for example, intravenous administration, intraperitoneal administration, intramuscular administration, subcutaneous administration, or topical administration. Furthermore, oral administration, rectal administration, inhalation administration, intranasal administration, or the like may be possible.

The appropriate dose of the pharmaceutical composition of the present invention varies depending on factors such as a formulating method, manner of administration, patient's age, body weight, gender, severity of disease, food, time of administration, route of administration, excretion rate, and response sensitivity, and an ordinarily skilled practitioner can easily judge and prescribe the dose effective for the desired treatment or prevention.

The pharmaceutical composition of the present invention is formulated using a pharmaceutically acceptable carrier and/or excipient according to the method that is easily conducted by a person having ordinary skills in the art to which the present invention pertains, and the composition of the present invention may be prepared into a unit dosage form or may be inserted into a multi-dose container. Here, the dosage form may be a solution, a suspension, or an emulsion in an oily or aqueous medium, and may further include a dispersing agent or a stabilizer.

In accordance with still another aspect of the present invention, there is provided a method for preparing a bilirubin derivative particle comprising a metal and a bilirubin derivative, the method including the steps of:

(a) conjugating bilirubin to a hydrophilic molecule to prepare a bilirubin derivative; and (b) coordinating the bilirubin derivative and a metal to prepare a bilirubin derivative particle having the metal encapsulated therein.

According to an embodiment of the present invention, step (b) may include the following steps:

(b-1) preparing a particles composed of the bilirubin derivative; and (b-2) encapsulating the metal in the particle composed of the bilirubin derivative.

According to another embodiment of the present invention, the preparation of the particle composed of the bilirubin derivative and the encapsulation of the metal may be performed at the same time in step (b).

The method for preparing the particles containing a bilirubin derivative and a metal of the present invention will be described by steps.

(a) Conjugating Bilirubin to a Hydrophilic Molecule to Prepare a Bilirubin Derivative Bilirubin is conjugated to a hydrophilic molecule to prepare hydrophilic or amphiphilic bilirubin. Specifically, the carboxyl groups of bilirubin are activated by using 1-ethyl-3-(3-dimethylaminopropyl)carbodiimide (EDC) or EDC/NHS, and the conjugation of the bilirubin with a hydrophilic molecule having an amine group (—$NH_2$) through amide bonding is introduced. The hydrophilic molecule conjugated to the bilirubin includes the above-described hydrophilic molecules, and may have an amine group or may be modified to have an amine group.

Also, a carboxyl group of the bilirubin is conjugated through an esterfication with a hydroxyl group of the hydrophilic molecule.

According to an embodiment, bilirubin is dissolved in an organic solvent (e.g., dimethyl sulfoxide (DMSO)), and in order to activate a carboxyl group of the bilirubin to induce a desired reaction, EDC is added, followed by reaction for 10 minutes at room temperature. Thereafter, a hydrophilic molecule having an amine group at an end thereof (e.g., polyethylene glycol) is added, followed by reaction for a period of time, to synthesize a hydrophilic molecule-conjugated bilirubin derivative. Last, a final bilirubin derivative having an amide bond generated from a reaction between a carboxyl group and an amine group is purely separated and extracted from a byproduct through a silica column.

(b) Coordinating the Bilirubin Derivative and a Metal to Prepare a Bilirubin Derivative Particle Having the Metal Encapsulated Therein In the present step, actually practicable nanoparticle forms are prepared by inducing coordinate bonding of the amphiphilic bilirubin derivative (e.g., PEGylated bilirubin) extracted in step (a) with various metal particles or metal ions. The following specific preparation method is merely provided for exemplary illustration, but is not limited to the scope of the present invention.

(b-1) Preparing Bilirubin Nanoparticle Composed of Bilirubin Derivative

Specifically, the hydrophilic molecule-conjugated amphiphilic bilirubin derivative is dissolved in an organic solvent, such as chloroform or dimethyl sulfoxide, followed by drying under nitrogen gas conditions, to thereby form a lipid film layer. Thereafter, the formed lipid film layer of the bilirubin derivative is hydrated with an aqueous solution to thereby obtain self-assembled bilirubin nanoparticles.

(b-2) Encapsulating a Metal Particle or Metal Ion in the Particle Composed of Bilirubin Derivative When various aqueous solutions of metal particles or metal ions are mixed to react with an aqueous solution of the bilirubin nanoparticles obtained in step (b-1), desired metals are encapsulated in the bilirubin derivatives or complexes are formed without other additives, such as chelators or linkers. Unreacted metal ions and the like can be removed by size-exclusion column or dialysis, thereby finally obtaining desired reaction products.

The step of encapsulating the metal in the bilirubin derivative particle of the present invention (b-2) can be performed simultaneously with the step of preparing the bilirubin nanoparticle composed of the bilirubin derivative (b-1).

That is, instead of hydrating the lipid film layer of bilirubin derivative with an aqueous solution to prepare bilirubin nanoparticles (step (b-1)) and then mixing an aqueous solution of metal ions therewith (step (b-2)), the lipid film layer of bilirubin derivative is directly mixed with and hydrated with the aqueous solution of metal ions, so that a metal ion is encapsulated in the bilirubin derivative particle, like in the case where steps (b-1) and (b-2) are performed sequentially. However, the encapsulation efficiency of metal ions is excellent in the case where, by performing steps (b-1) and (b-2) sequentially, the aqueous solution of bilirubin nanoparticles is prepared and then the aqueous solution of metal ions is mixed therewith to form a complex.

A method of coating metal nanoparticles (e.g., iron nanoparticles, gold nanoparticles, etc.) with the bilirubin derivative requires a slightly different procedure from a method of encapsulating metal ions.

According to another embodiment of the present invention, a particle in which a metal ion is coated with a single layer of the bilirubin derivative of the present invention can be formed.

Specifically, as for a method of coating an iron nanoparticle with a single layer of bilirubin derivative, a hexane solution containing iron nanoparticles (SPIONs) dissolved therein is added into the aqueous solution of bilirubin nanoparticles obtained in step (b) to form an interface portion between a water layer and an organic solvent layer, and then artificial pressure is applied to the interface portion using a sonicator to mix the two layers, so that an oleic acid layer, which has been originally coated on the iron nanoparticles (SPIONs), is separated by a ligand exchange method, and instead, gold nanoparticles are coated through a chelation reaction of a carboxyl group of the bilirubin derivative (e.g., PEGylated bilirubin) with a core portion of the iron nanoparticle (SPION).

According to another embodiment of the present invention, a particle in which clustered metal particles are coated with the bilirubin derivative of the present invention can be formed.

Specifically, a bilirubin derivative (e.g., PEGylated bilirubin) dissolved in an organic solvent (e.g., chloroform) is mixed with SPIONs dissolved in methanol, and then the organic solvent is dried under nitrogen gas conditions, thereby forming a lipid film layer. The formed lipid film layer is hydrated to form a cluster form of SPIONs.

Pure SPIONs can be isolated as a final reaction product through a magnet isolation method using a magnet after the above procedures.

According to still another embodiment of the present invention, as for a method of coating a gold nanoparticle with a bilirubin derivative, the bilirubin derivative obtained in step (a) is dissolved in water but not an organic solvent, followed by direct reaction with an aqueous solution containing gold nanoparticles dissolved therein for a predetermined period of time. In a similar principle with respect to SPION coating, the bilirubin derivative, instead of citrate originally coated on the gold nanoparticle, is coated with surrounding the nanoparticle core portion.

In accordance with another aspect of the present invention, there is provided a composition for detection of reactive oxygen species (ROS), the foregoing composition containing the bilirubin derivative particles of the present invention.

As used herein, the reactive oxygen species refers to an oxygen species that are more reactive and have higher activity compared with usually present ground-state triplet oxygen ($^3O_2$).

According to an embodiment of the present invention, the reactive oxygen species includes superoxide ($O^{2-}$), hydrogen peroxide ($H_2O_2$), hydroxy radical (OH), and singlet oxygen ($^1O_2$). In addition, the reactive oxygen species includes an organic hydroperoxide (RCOO), an alkoxy radical (RO), peroxy radical (ROO.), or ozone ($O_3$), and nitrogen dioxide ($NO_2$)

In accordance with another aspect of the present invention, there is provided a sensor for detection of reactive oxygen species (ROS), the sensor containing the foregoing bilirubin derivative particles of the present invention.

According to a specific embodiment of the present invention, the sensor for detection is not particularly limited, and may be any device that can detect a physico-chemical change due to the contact between the bilirubin derivative particles of the present invention and reactive oxygen species and can be used in the art, as described later.

In accordance with still another aspect of the present invention, there is provided a method for detection of reactive oxygen species, the method including:

(a) contacting a suspension containing the bilirubin derivative particles of the present invention with a sample containing reactive oxygen species; and (b) comparing and analyzing a change of the suspension before and after the contact with the sample with a control group.

The method for detection of reactive oxygen species of the present invention will be described by steps.

(a) Contacting a Suspension Containing the Bilirubin Derivative Particles of the Present Invention with a Sample Containing Reactive Oxygen Species In the step, a suspension containing the bilirubin derivative particles of the present invention is contacted with a sample, in which reactive oxygen species is to be detected, to thereby perform a reaction of the bilirubin derivative particles in the suspension and the reactive oxygen species. The bilirubin derivative of the present invention is reactive with reactive oxygen species. Therefore, when the bilirubin derivative in the suspension is contacted with the reactive oxygen species in the sample, the bilirubin derivative forming a shell of the metal particle is separated from the metal particle due to the reaction of the bilirubin derivative with the reactive oxygen species. As a result, hydrophobic metal particles meet each other to form an aggregate or a precipitate.

As used herein, the sample includes, but is not limited to, human or animal urine, saliva, blood (plasma, serum, blood cells), and tissues (tissues of lesions, such as liver, pancreas, and skin). The sample also includes other substances, such as a solution containing a compound generating reactive oxygen species.

(b) Comparing and Analyzing a Change of the Suspension Before and after the Contact with the Sample with a Control Group In the step, a change of the suspension, resulting from the reaction of the bilirubin derivative with reactive oxygen species in the sample, is compared and analyzed with a control group. The control group means the changes of the suspension according to the kind and concentration of reactive oxygen species, the changes being i) previously measured or ii) measured simultaneously with step (a) for different kinds and different concentrations of reactive oxygen species.

According to an embodiment of the present invention, the change of the suspension in step (b) includes the presence or absence of precipitation of bilirubin derivative particles, absorbance according to wavelength, transparency of the suspension, the concentration of metal ions in the suspension, and the intensity of MR image signal, but is not limited thereto.

The method of the present invention commonly uses the above-described bilirubin derivative particles of the present invention and the composition or apparatus including the particles, and thus the descriptions of the overlapping contents therebetween are omitted to avoid excessive complication of the present specification.

In accordance with another aspect of the present invention, there is provided a method for image diagnosis, the method including a step of administering a composition containing bilirubin derivative particles to a subject.

In accordance with another aspect of the present invention, there is provided a method for cancer treatment, the method including a step of administering a composition containing bilirubin derivative particles to a subject.

In accordance with still another aspect of the present invention, there is provided a method for treatment and diagnosis of an inflammatory disease, the method including a step of administering a composition containing bilirubin derivative particles to a subject.

As used herein, the term "administration" or "administer" refers to the direct administration of a therapeutically or diagnostically effective amount of the composition of the present invention to a subject (an object) in need of the composition, thereby forming the same amount thereof in the body of the subject.

The term "therapeutically effective amount" of the composition refers to the content of the composition, which is sufficient to provide a therapeutic or prophylactic effect to a subject, to which the composition is to be administered, and thus the term has a meaning including "prophylactically effective amount". The term "diagnostically effective amount" of the composition refers to the content of the composition, which is sufficient to provide a diagnostic effect to a subject to which the composition is to be administered.

As used herein, the term "subject" includes, but is not limited to, humans, mice, rats, guinea pigs, dogs, cats, horses, cows, pigs, monkeys, chimpanzees, baboons, or rhesus monkeys. Specifically, the subject of the present invention is a human.

The method for image diagnosis, the method for cancer treatment, and the method for treatment and diagnosis of an inflammatory disease, of the present invention, include a step for administering the composition for each purpose containing the bilirubin derivative particles according to an aspect of the present invention, and thus the descriptions of overlapping contents therebetween are omitted to avoid excessive complication of the specification due to repetitive descriptions thereof.

Advantageous Effects

Features and advantages of the present invention are summarized as follows.

(i) The present invention provides hydrophilic bilirubin derivative particles containing a metal, a use thereof, and a preparation method therefor.

(ii) The bilirubin derivative particles of the present invention form coordinate bonds with various metals, and thus can be used in MR diagnosis, CT diagnosis, photo-acoustic diagnosis, PET diagnosis, or optical diagnosis.

(iii) The bilirubin derivative particles of the present invention exhibit, in addition to the diagnostic use, anti-inflammatory activity and anticancer activity due to antioxidative activity and anticancer activity of bilirubin itself, and thus have a concept of theranostics, in which the bilirubin derivative particles can be for therapeutic uses for treatment of both an inflammatory disease and a cancer disease.

(iv) The bilirubin nanoparticles of the present invention are degraded by the stimulation of light or reactive oxygen species, thereby releasing a drug encapsulated therein to the outside.

Furthermore, the bilirubin derivative particles of the present invention is reactive with reactive oxygen species, and thus can be used as a composition, sensor, kit, contrast agent, or device for detecting the kind and concentration of reactive oxygen species.

DETAILED DESCRIPTION

Hereinafter, the present invention will be described in detail with reference to examples. These examples are only for illustrating the present invention more specifically, and it will be apparent to those skilled in the art that the scope of the present invention is not limited by these examples.

EXAMPLES

Example 1: Preparation of Bilirubin Derivative (PEG-BR) Particles of the Present Invention 1-1. Preparation of Bilirubin Derivative (PEG-BR)

The present inventors prepared a bilirubin derivative in which polyethylene glycol as a hydrophilic molecule is conjugated to bilirubin, as a previous step for preparing a bilirubin derivative particles containing bilirubin and a metal, using a complexation effect of bilirubin.

First, bilirubin was dissolved in dimethyl sulfoxide (DMSO), and then, in order to activate a carboxyl group present in bilirubin to induce a desired reaction, an appropriate amount of 1-ethyl-3-(3-dimethylaminopropyl)carbodiimide (EDC) was added thereto, followed by reaction at room temperature for 10 minutes. Then, polyethylene glycol having an amine group at an end thereof was added thereto, followed by reaction for a predetermined period of time, thereby synthesizing a bilirubin derivative in which a carboxyl group of bilirubin is conjugated to an amine group of polyethylene glycol through an amide bond. Last, the finally prepared bilirubin derivative was purely isolated and extracted from byproducts through a silica column.

1-2. Preparation of Bilirubin Derivative (PEG-BR) Particles

The polyethylene glycol-conjugated amphiphilic bilirubin derivative, which was prepared in example 1-1 above, was dissolved in an organic solvent, such as chloroform or dimethyl sulfoxide, followed by drying under nitrogen gas conditions, to thereby form a lipid film layer. The prepared lipid film layer of bilirubin derivative was hydrated with an aqueous solution to prepare self-assembled bilirubin particles dissolved in the aqueous solution.

Example 2: Preparation of Bilirubin Derivative Particles Containing Metal (Metal Ion) of the Present Invention—1

Figure 2:
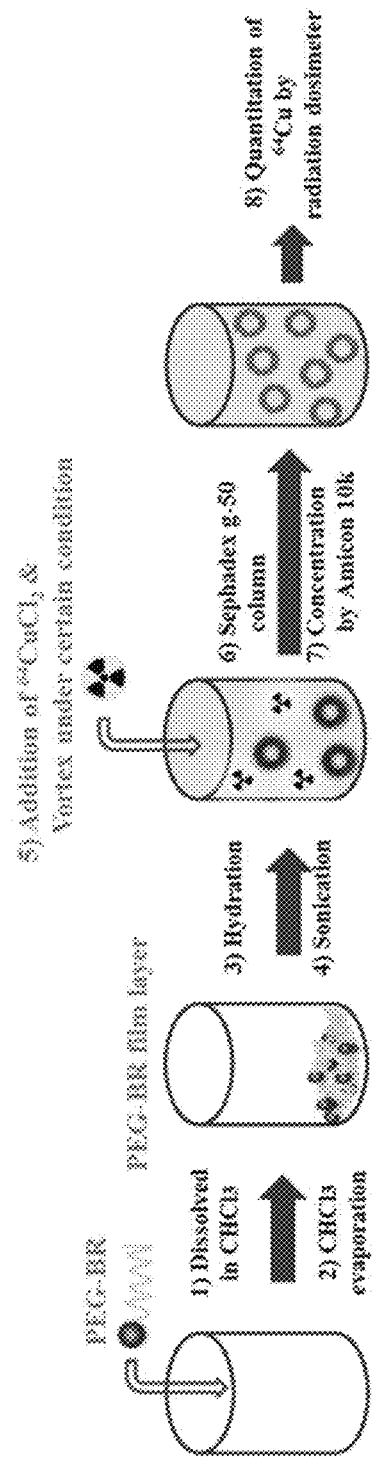
FIG. 2 shows a preparation procedure for bilirubin derivative particles of the present invention and a labeling procedure using the radioactive isotope $^{64}$Cu for the use of PET imaging.

2-1. Preparation of Bilirubin Derivative Particles Containing $^{64}Cu$ Ion as Radioactive Isotope and In Vivo PET Imaging Thereof In order to investigate the metal ion encapsulation effect of the bilirubin derivative particles of the present invention, the following experiment was conducted. An aqueous solution of a small amount of radioactive isotope $^{64}CuCl_2$, which is used in PET image diagnosis, was mixed with an aqueous solution of the bilirubin derivative particles prepared in example 1 without a separate additive. Then, a reaction occurred very intensively and rapidly to load $^{64}Cu$ ions with only a reaction time of about 30 minutes (FIG. 2).

Figure 3:
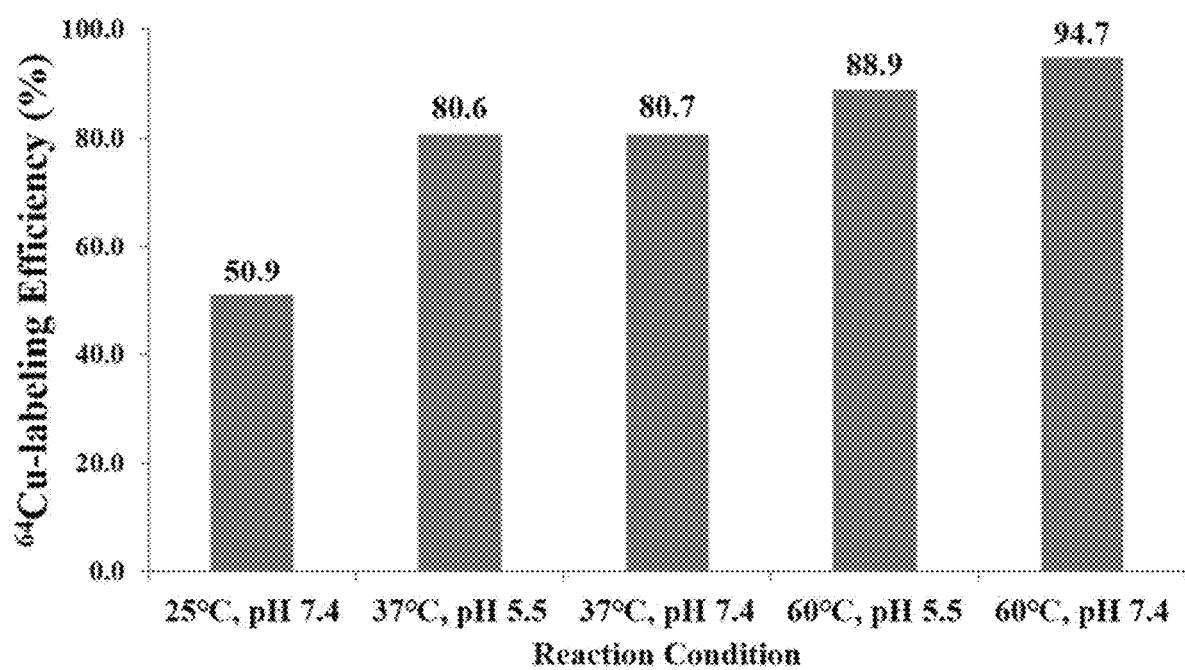
FIG. 3 shows labeling efficiency according to pH and temperature in order to investigate reaction conditions for optimizing radioactive labeling efficiency.

In addition, in order to investigate how great active the bilirubin derivative particles of the present invention are, the free $^{64}Cu$ not contained in bilirubin was removed using a size exclusion column, and then quantified with a radiation dosimeter. Meanwhile, the reaction methods under other pH and temperature conditions in the 64Cu chelation were optimized to be almost identical to the physiological environment (37° C., pH 7.4) (FIG. 3).

The coordinate bond between the $^{64}Cu$ ion and the bilirubin derivative of the present invention may be formed by the $^{64}Cu$ ion and a pyrrole group, lactam group, or carboxyl group of bilirubin, and an exemplary expression thereof is shown in chemical formula 2.

[Chemical Formula 2]

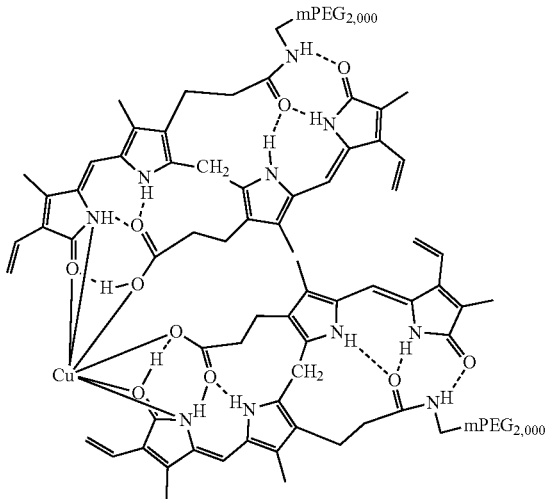

Figure 4:
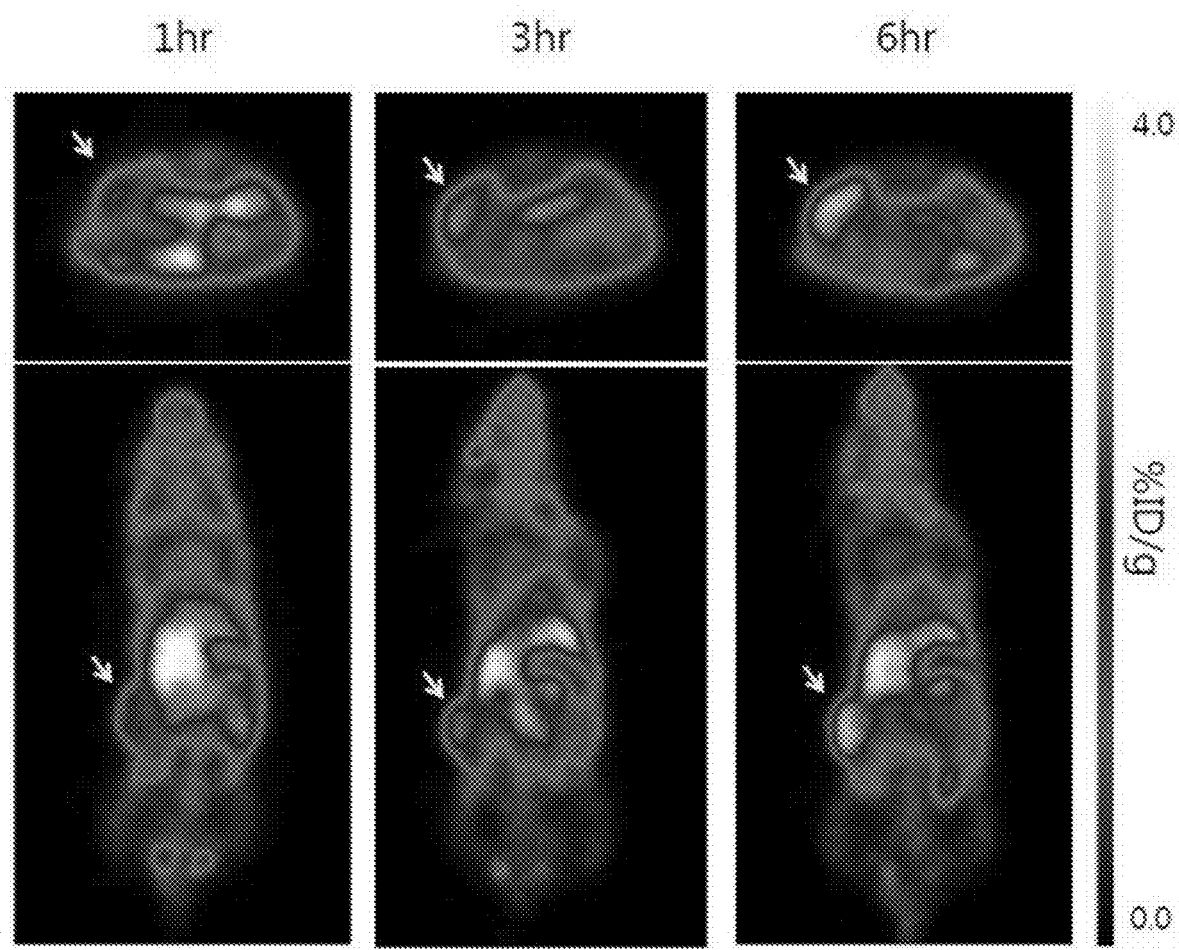
FIG. 4 shows representative micro-PET images of PC-3 tumor (yellow arrows)-retaining mice 1, 3, and 6 hr after intravenous injection of $^{64}$Cu-bilirubin particles (axial images, upper panels; and coronal images, lower panels).

In addition, the bilirubin derivative particles, in which the $^{64}$Cu ion is coordinated by the bilirubin derivative (PEG-BR) particles prepared in example 1 above, were injected into rats with a tumor, and in vivo performance thereof was preliminarily investigated by PET imaging. As a confirmation results, the $^{64}$Cu-bilirubin particles clearly visualized the tumor in a time-dependent manner, and the highest tumor uptakes at 1 h, 3 h and 6 h after injection were about 2.15, 2.81, and 3.75% injected dose (ID)/g, respectively (FIG. 4).

Figure 5A:
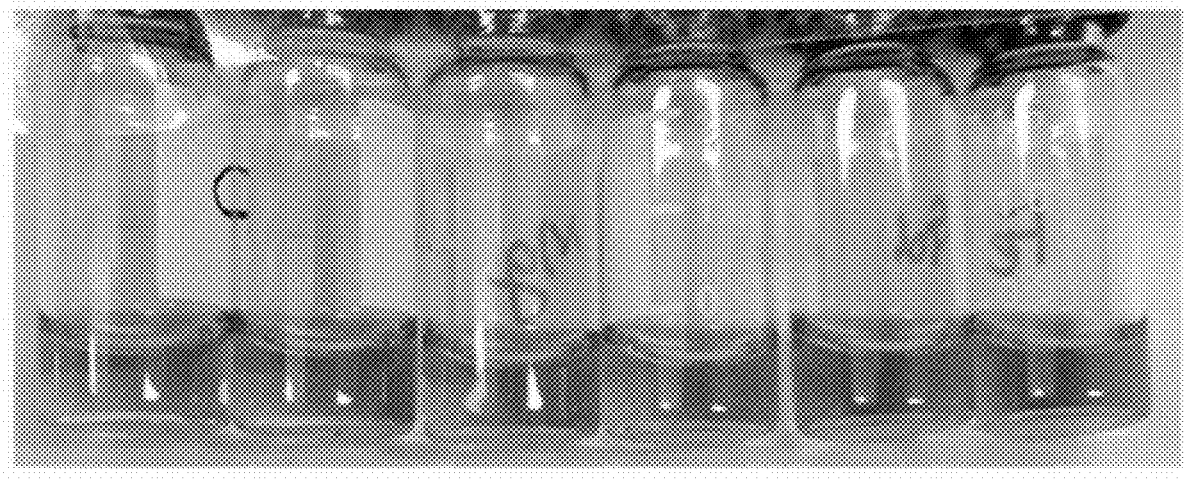
FIG. 5a illustrates the colorimetric measurement in the reaction of PEG-bilirubin and metal ions and provides images of a suspension of bilirubin particles before (upper panel) and after (lower panel) the reaction with particular metal ions.
Figure 5A:
Figure 5B:
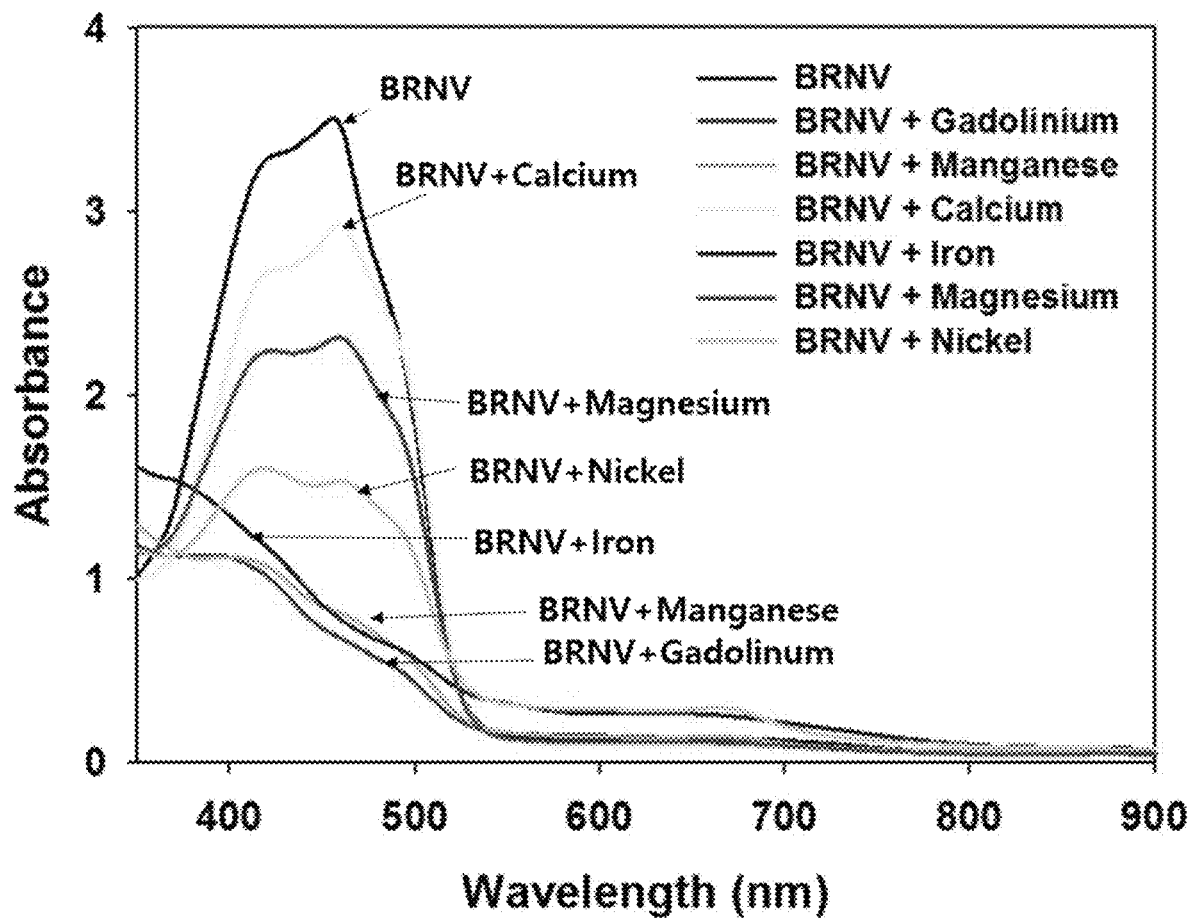
FIG. 5b illustrates the colorimetric measurement in the reaction of PEG-bilirubin and metal ions and shows UV/Vis spectra for a suspension of bilirubin particles before and after the reaction with particular metal ions.

2-2. Preparation of Bilirubin Derivative Particles Containing Various Metal (Ni, Mn, Gd, Mg, Ca, Fe) Ions In order to investigate the encapsulation effect (chelating effect) of the bilirubin derivative particles of the present invention with respect to various metal ions, the possibility of coordination complex formation for six metals (Ni, Mn, Gd, Mg, Ca, and Fe) was examined. As for an experimental method, an aqueous solution containing each of the metal ions was added to an aqueous solution of the bilirubin particles prepared in example 1, followed by mixing, as in example 2-1 above. After a certain reaction time, all the metals, especially transition metals, exhibited color changes (Ni=Fe>Gd=Mn), which were distinctive when compared with the color changes of Mg and Ca (FIG. 5a). In addition, the respective metals, even magnesium and calcium groups, showed various absorbance pattern changes compared with general particle solutions (FIG. 5b).

The above results that, after forming coordinate bonding with particular metal ions, the bilirubin particle solution showed color changes from the original yellow color thereof or showed a displacement or change in particular absorbance pattern, may provide the applicability of novel PEGylated bilirubin beyond previous biomedical application fields Therefore, it could be confirmed that the ability of the bilirubin derivate particles of the present invention to form a metal-organic coordination complex for various metals can be used for various applications including a metal ion detection system.

Example 3: Preparation of Bilirubin Derivative Particles Containing Metal (Metal Nanoparticles) of the Present Invention—2

3-1. Preparation of Bilirubin Derivative Particles Containing Single Superparamagnetic Iron Oxide Nanoparticle (SPION)

Figure 6A:
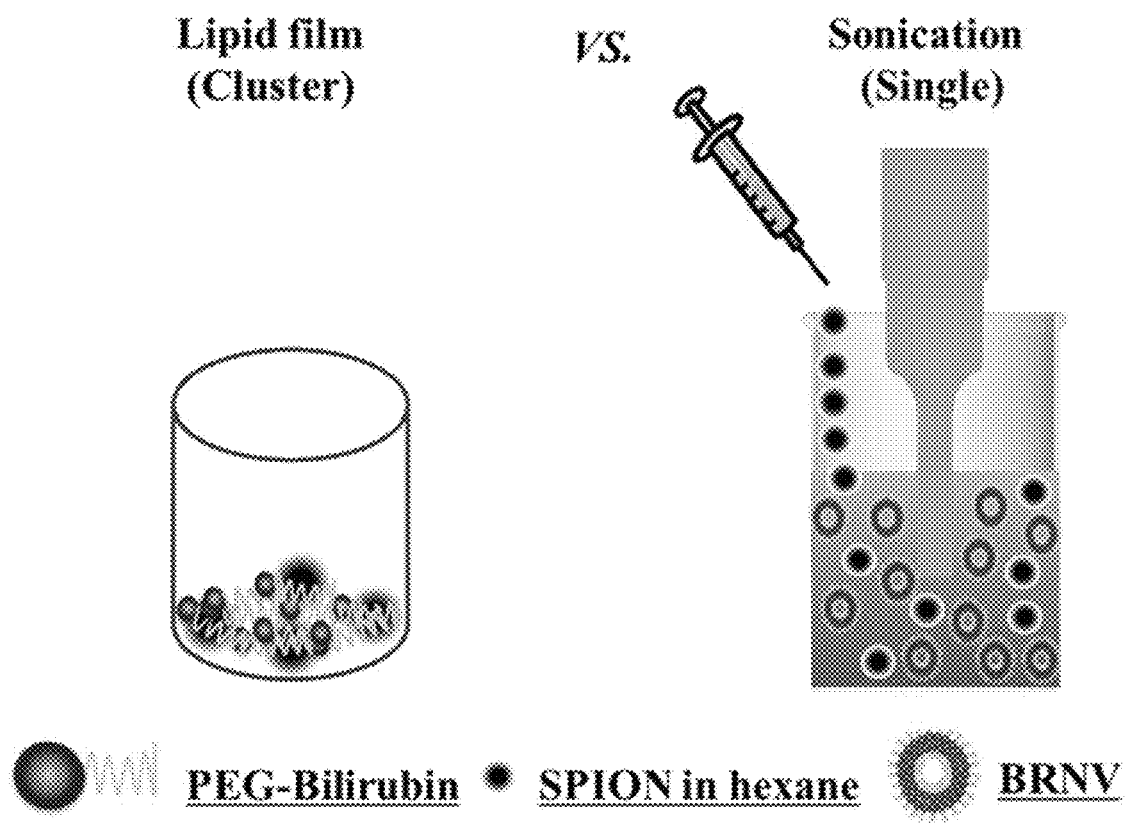
FIG. 6a shows the preparation of an iron oxide-based MR probe using PEG-bilirubin. (1) In the lipid film method on the left side, the bilirubin derivative particles having a metal encapsulated therein of the present invention are produced such that clustered iron oxide is placed at the center and the PEG-bilirubin layer surrounds the iron oxide. (2) In the sonication method on the right side, uniform iron oxide nanoparticles coated with the PEG-bilirubin layer are produced.
Figure 6B:
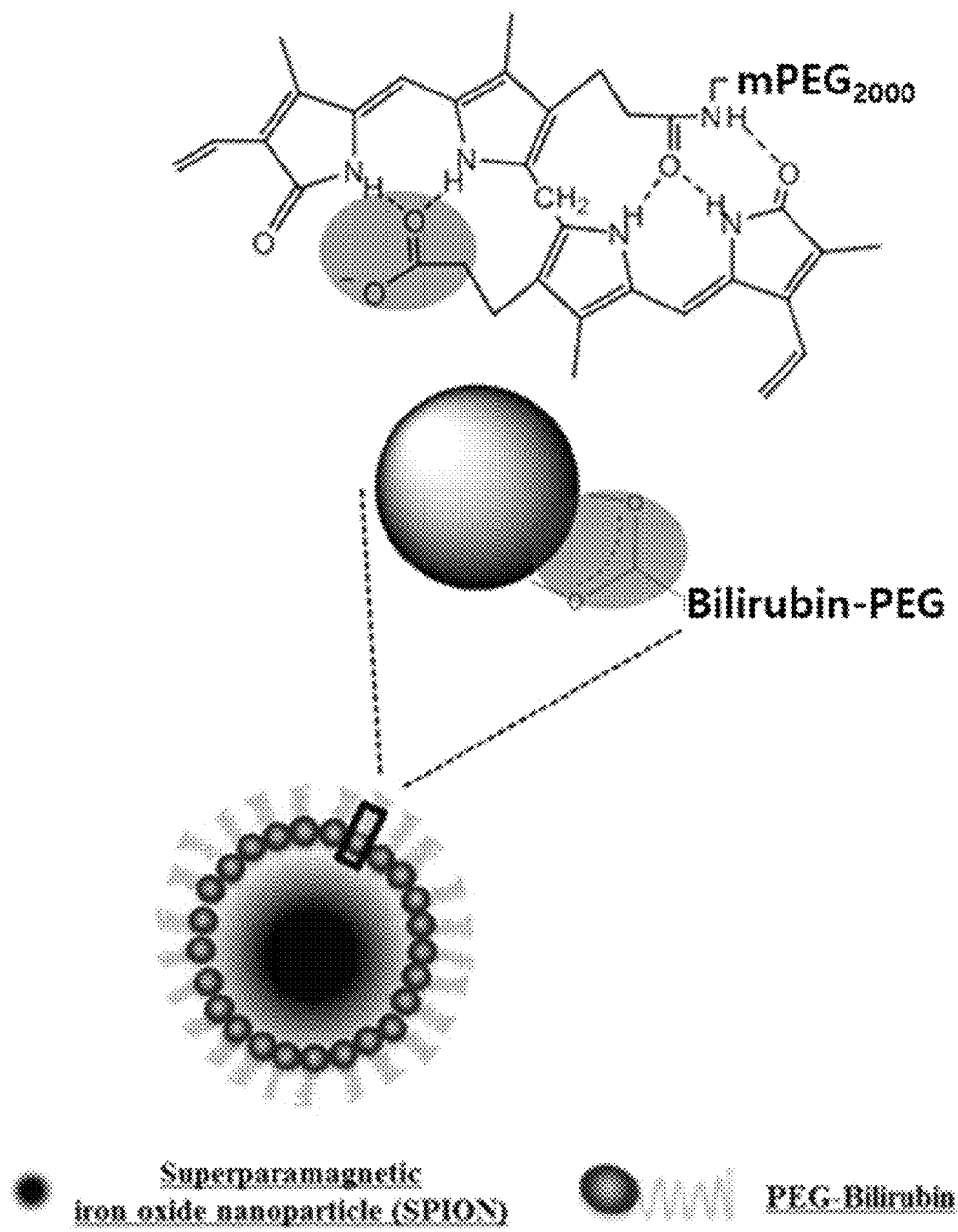
FIG. 6b shows the principle of coordinate bonding of PEG-bilirubin and superparamagnetic iron oxide.

In order to coat superparamagnetic iron oxide nanoparticles (SPIONs) with the bilirubin derivative of the present invention, a hexane solution containing superparamagnetic iron oxide nanoparticles (SPIONs) dissolved therein was added to the aqueous solution of the bilirubin nanoparticles prepared in example 1 above, to thereby form an interface portion through the separation of a water layer and a hexane layer. The artificial pressure is applied to the interface portion using a sonicator to mix the two layers for a predetermined period of time, thereby preparing particles in the form in which the bilirubin derivative (PEG-BR) is coated on surfaces of the iron nanoparticles (FIG. 6a). The above reaction is on the basis of a principle of ligand exchange, in which an oleic acid layer, which is originally coated on the iron nanoparticle (SPIONs), is separated, and instead, through a chelation reaction of the carboxyl group of the bilirubin derivative (PEG-BR) and a core portion of the iron nanoparticles (SPIONs), metal nanoparticles were coated (FIG. 6b).

3-2. Preparation of Bilirubin Derivative Particles Containing Clustered Form of Superparamagnetic Iron Oxide Nanoparticles (SPIONs)

In order to prepare particles in the form in which metal particle clusters are coated with a bilirubin derivative, SPION particles dissolved in methanol were mixed with bilirubin derivative (PEG-RB) dissolved in an organic solvent (e.g., chloroform), instead of adding metal particles dissolved in an organic solvent to an aqueous solution containing a bilirubin derivative (PEG-BR) dissolved therein as in example 3-1. Thereafter, the organic solvent was dried under nitrogen gas conditions to form a lipid film layer. Last, the formed lipid film layer was hydrated to form a cluster form of SPIONs. Pure SPIONs were isolated through a magnet after passing through the above procedures, and a cluster form of SPIONs prepared thereby was isolated as a final reaction product.

Figure 6C:
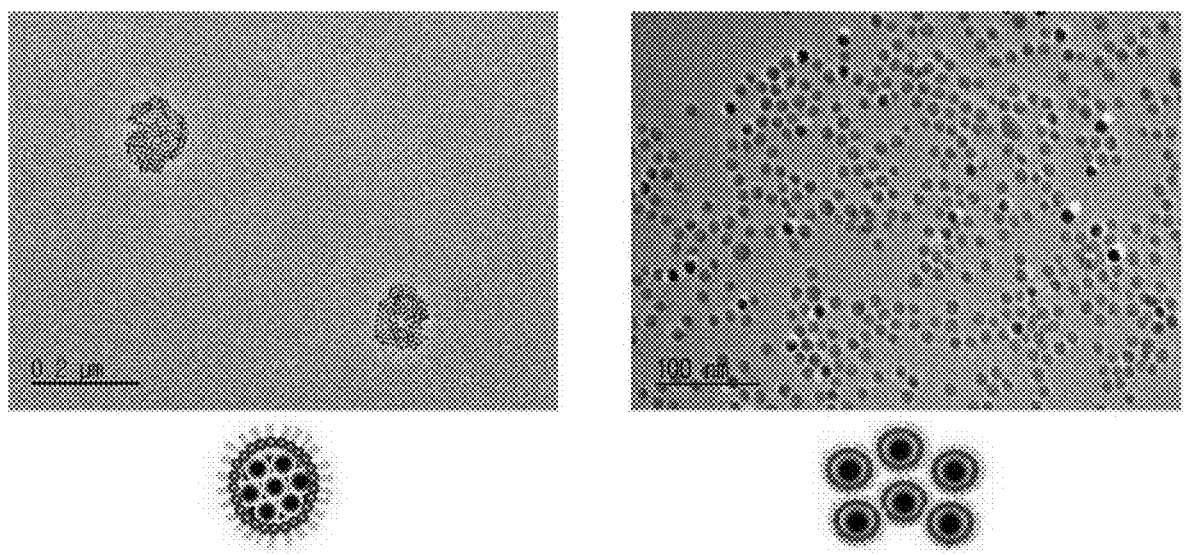
FIG. 6c provides representative TEM images showing clustered iron oxide nanoparticles with a PEG-bilirubin shell (left side) and uniformly distributed iron oxide nanoparticles with PEG-bilirubin shells (right side).

The present inventors confirmed from TEM images that two types of particles in examples 3-1 and 3-2 were successfully prepared using PEG-bilirubin shells (FIG. 6c).

3-3. Preparation of Bilirubin Derivative Particles Containing Gold Nanoparticle

In order to coat gold nanoparticles with a bilirubin derivative, the bilirubin derivative (PEG-BR) prepared in example 1-1 above was dissolved in water rather than an organic solvent, followed by immediate reaction with an aqueous solution containing gold nanoparticles dissolved therein for a predetermined period of time. The principle of the reaction is similar to the principle of SPION coating in example 3-1. The bilirubin derivative (PEG-BR), in substitution for a citrate layer, coated on the gold nanoparticles, was coated while surrounding a nanoparticle core.

Example 4: ROS-Responsiveness of Bilirubin Derivative Particles Containing Metal (Metal Nanoparticles) of the Present Invention 4-1. MRI Phantom Study of Bilirubin Derivative Particles Containing SPION The present inventors conducted the MRI phantom study in order to study characteristics of SPION coated with PEG-bilirubin in the form of mono-distribution particles.

Figure 7:
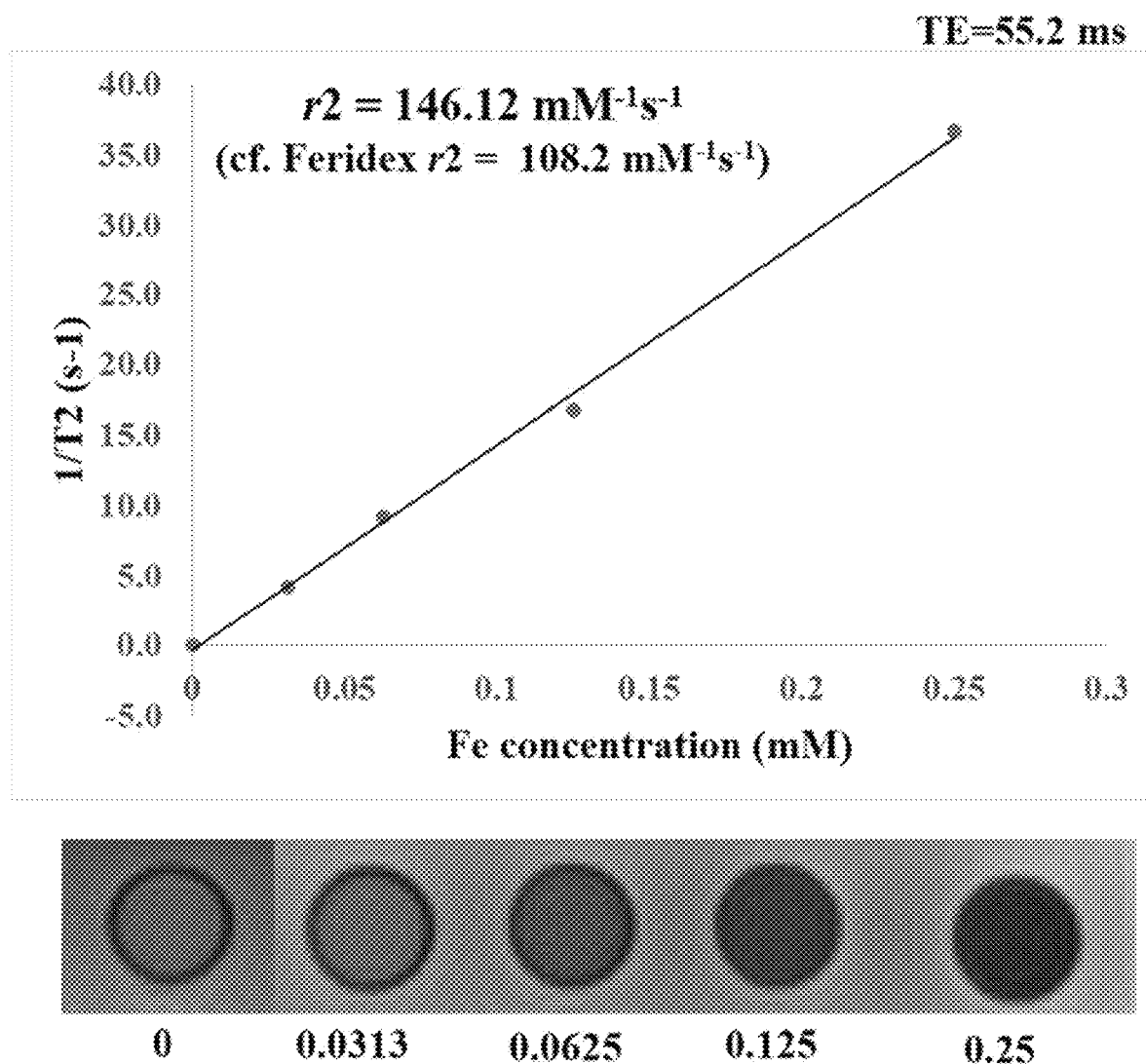
FIG. 7 shows the features of PEG-bilirubin coated SPIONs and provides the T2-weighted MR phantom images of PEG-bilirubin coated SPIONs in an aqueous solution and the T2 relaxation rate as a function of ion concentration.

First, as a result of comparing phantom images of the bilirubin derivative (PEG-BR) coated SPIONs of the present invention and Feridex, which is a clinically approved T2-weighted MR agent, the bilirubin derivative (PEG-BR) coated SPIONs of the present invention showed a more excellent relaxivity value than Feridex (FIG. 7).

Figure 8:
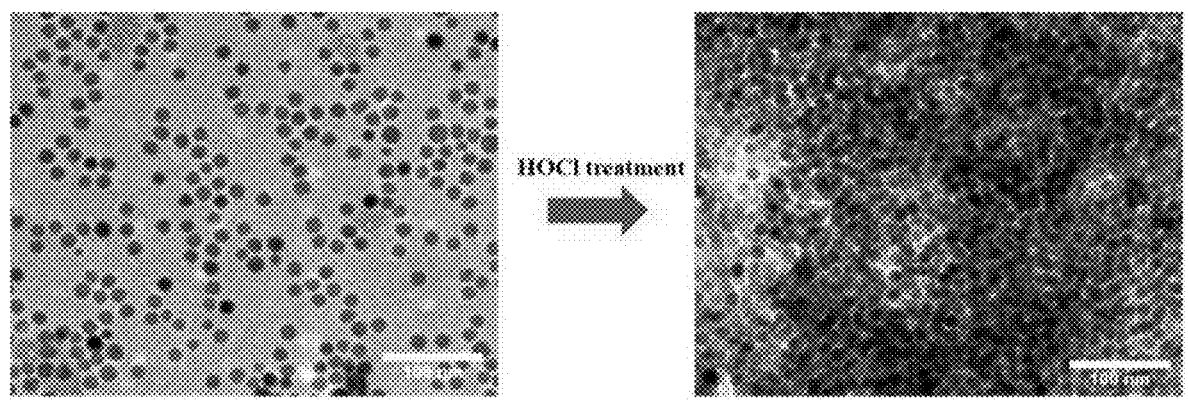
FIG. 8 shows the features of PEG-bilirubin coated SPIONs and provides TEM images of PEG-bilirubin coated SPIONs before and after ROS stimulation.
Figure 9A:
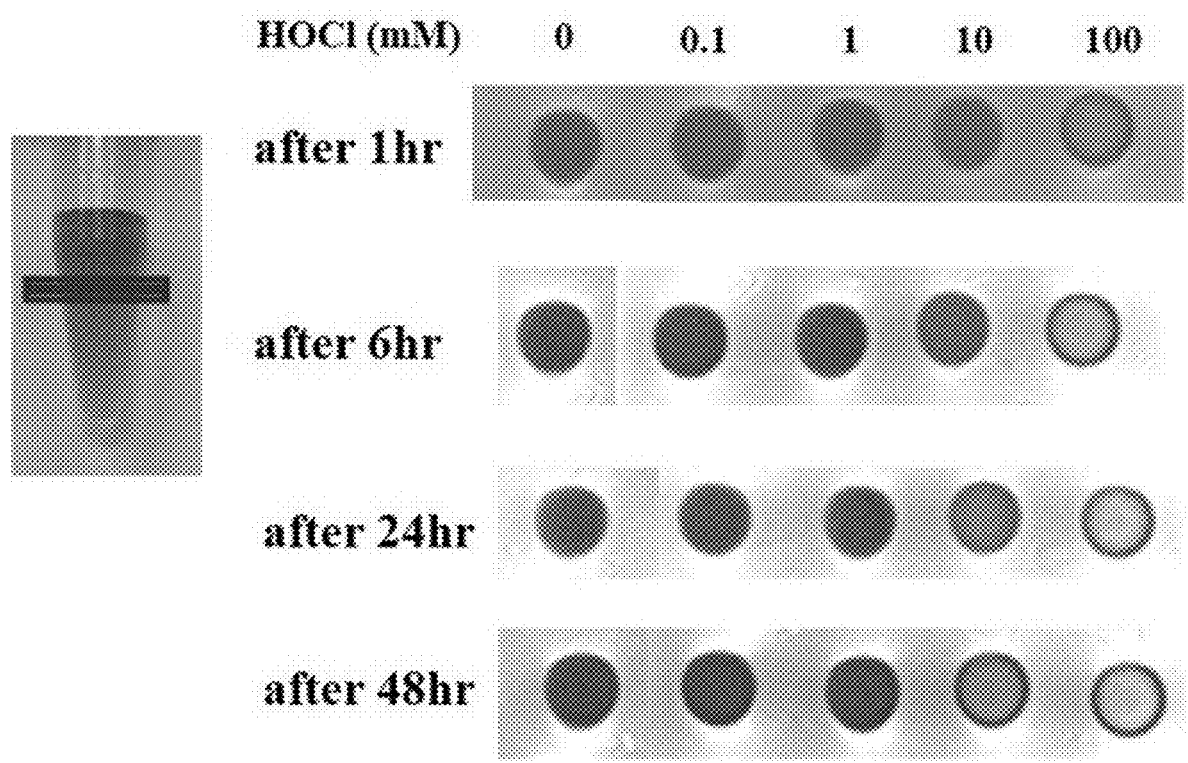
FIG. 9a shows the features of PEG-bilirubin coated SPIONs and provides sequential MR phantom images of ROS-responsiveness according to the ROS concentration, of PEG-bilirubin coated SPIONs.
Figure 9B:
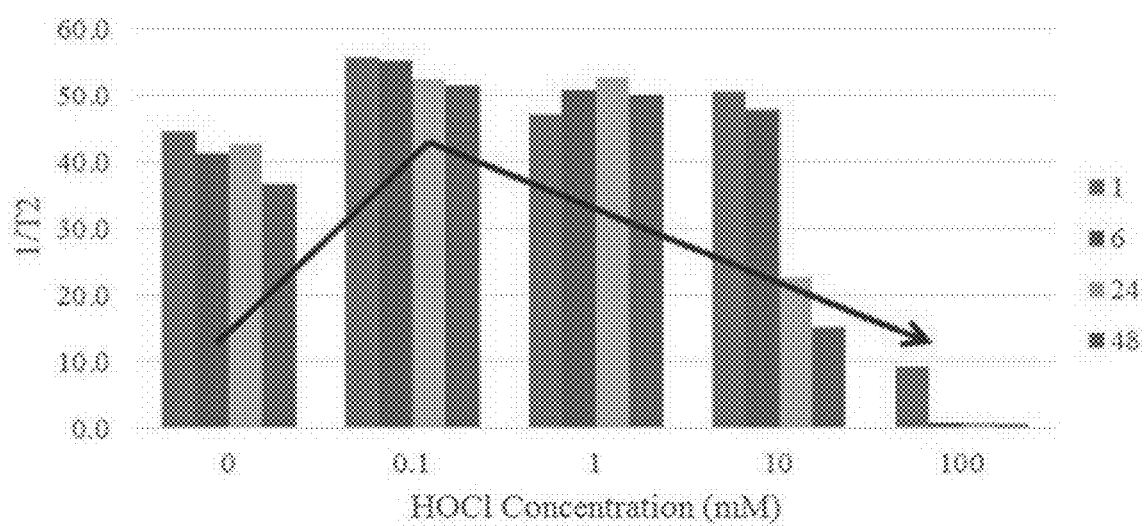
FIG. 9b shows the features of PEG-bilirubin coated SPIONs and provides a graph of T2 relaxation value change according to ROS concentration in PEG-bilirubin coated SPIONs.

In addition, when the bilirubin derivative (PEG-bilirubin) coated SPIONs were treated with hypochlorite as an ROX generator, the aggregation of PEG-bilirubin coated SPIONs was observed from the TEM image due to ROS-responsiveness inherent to bilirubin (FIG. 8). In addition, as predicted, the ROS-responsiveness by a gradual reduction of T2 signal, which is proportional to ROS concentration, due to the loss of hydrophilicity maintained by PEG-bilirubin was also indirectly validated in T2 MR phantom studies (FIGS. 9a and 9b). Such a SPION aggregation response can gradually increase the size of SPION, and thus can be a potent target for the therapeutic effect of magnetic hyperthermia.

4-2. In Vitro and In Vivo Tests for ROS-Responsiveness of Bilirubin Derivative Particles Containing SPION In order to investigate whether the PEG-bilirubin coated iron nanoparticles act and aggregate in response to ROS in vitro and in vivo, the following experiment was conducted using primary macrophages and macrophage strains, which are well known to phagocytize foreign pathogens through ROS and phagocytosis in inflammation conditions.

First, macrophages or peritoneal cavity was treated with lipopolysaccharides (LPS) to make an artificial inflammation condition, and then at the same time, subjected to treatment with PEG-bilirubin coated SPIONs and PEG-distearoylphosphatidylethanolamine (PEG-DSPE) coated SPIONs as a control group, and the phagocytosis patterns thereof were observed using an optical microscope and an MR phantom images.

Figure 10:
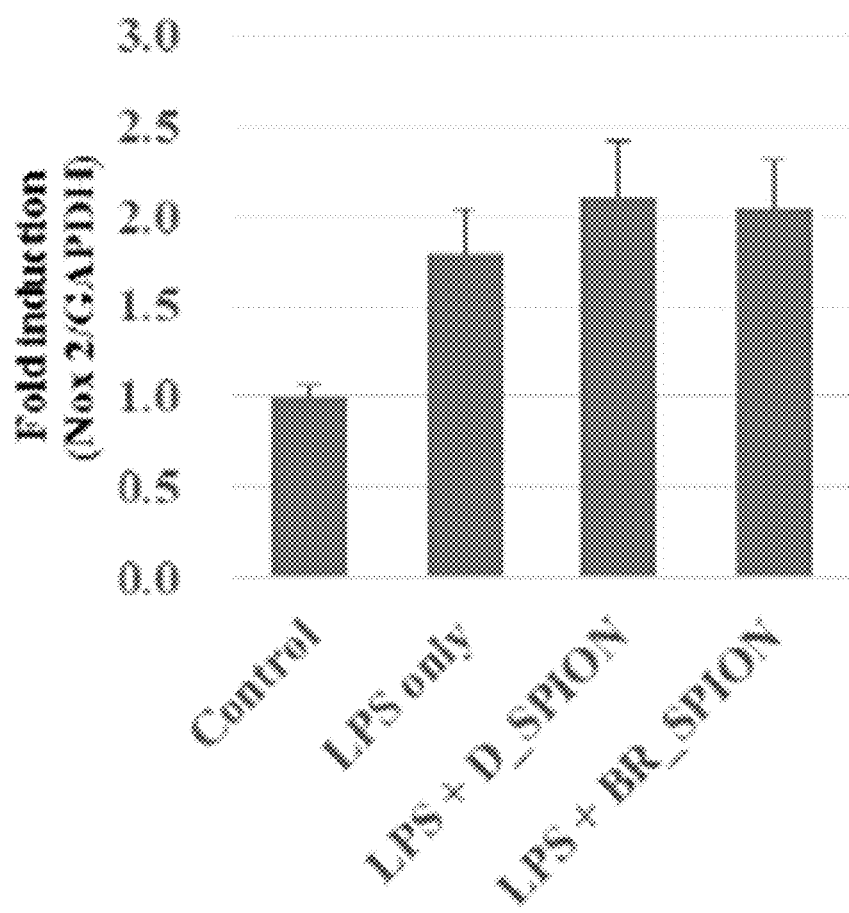
FIG. 10 shows the intra-macrophage expression level of Nox2 gene, measured by RT qPCR.

In order to investigate whether ROS was produced in the same amount in respective conditions, the intra-macrophage expression level of Nox2 gene, known as an ROS generation factor in the body, was measured by RT_qPCR. As a result, the PEG-DSPE and PEG-RB SPION groups showed almost similar expression levels of Nox2 gene, and produced similar amounts of ROS, which were higher compared with normal conditions (FIG. 10).

Figure 11A:
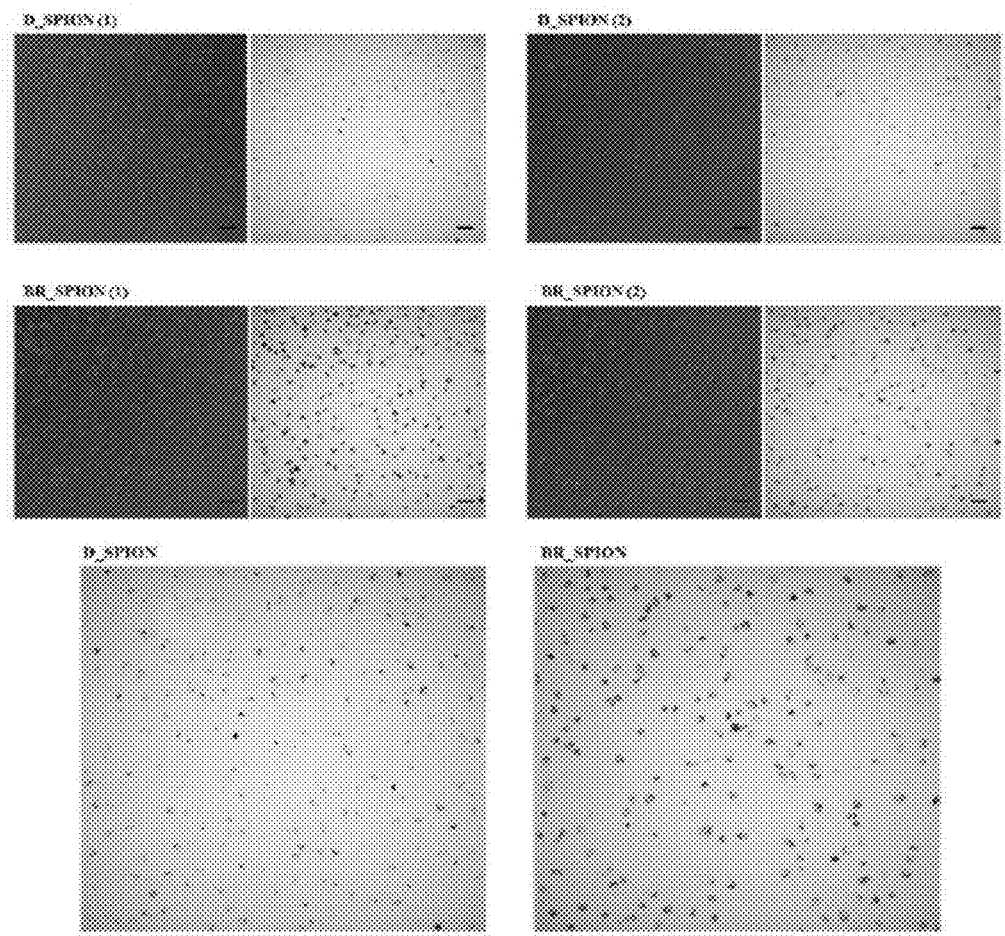
FIG. 11a shows the observation results, through an optical microscope, of the level of macrophage phagocytosis in PEG-DSPE coated SPION and PEG-BR SPION treatment groups under ROS production conditions.
Figure 11B:
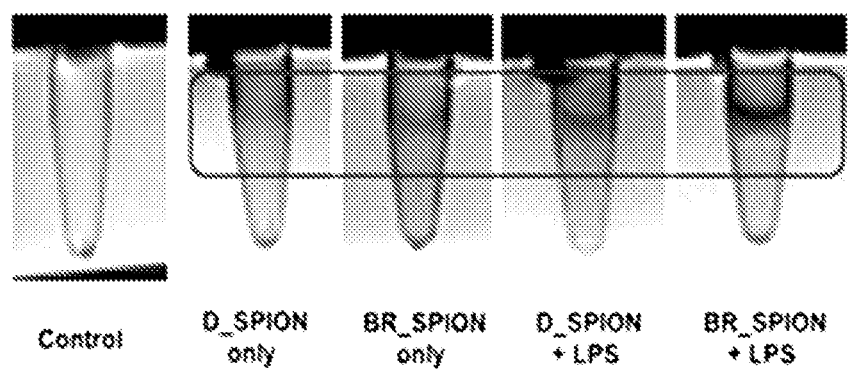
FIG. 11b shows the comparison, through MRI phantom experiment, of the level of macrophage phagocytosis in PEG-DSPE coated SPION and PEG-BR SPION treatment groups targeting the macrophages collected from the mouse peritoneal cavity.

In addition, the respective phagocytosis degrees of the PEG-DSPE coated SPION and PEG-BR coated SPION treatment groups in conditions of generating an equivalent amount of ROS were observed through an optoelectronic device. As a result of observation, the PEG-BR coated SPION treatment group showed higher phagocytosis levels than PEG-DSPE coated SPION treatment group as a control group (FIG. 11a, darker color being observed with increasing degree of phagocytosis). The MRI cell phantom studies for macrophages taken from the peritoneal cavity also showed the same pattern (FIG. 11b).

The above results are thought to result from the fact that the PEG-BR coating was peeled off from the PEG-BR coated SPION in response to ROS generated from the macrophage with stress increased by LPS treatment, so that the SPION cores aggregates, leading to increased phagocytosis, or the PEG-BR coated SPIONs also aggregate in cells in response to ROS after phagocytosis. Whereas, the PEG-DSPE coated SPIONs as a control group did not perform any reaction with ROS, and thus the activity of a relatively complete form of PEG-DSPE coated SPIONs per se is thought to be observed.

4-3. CT Phantom Studies and In Vitro and In Vivo Tests for ROS-Responsiveness of Bilirubin Derivative Particles Containing Gold Nanoparticle Gold nanoparticles have been widely studied as a CT contrast agent in a preclinical field. A surface of the gold nanoparticle coated with citric acid, like SPION, may be substituted with PEGylated bilirubin (PEG-BR) by coordinate boning. The successful binding of the PEGylated bilirubin to the gold nanoparticle was confirmed through TEM images and CT phantom images, and the UV-Vis wavelength change after chelation and ROS-responsiveness of the gold nanoparticle coated with bilirubin was investigated by comparing and observing the gold nanoparticle coated with PEGylated thiol as a control group.

Figure 12:
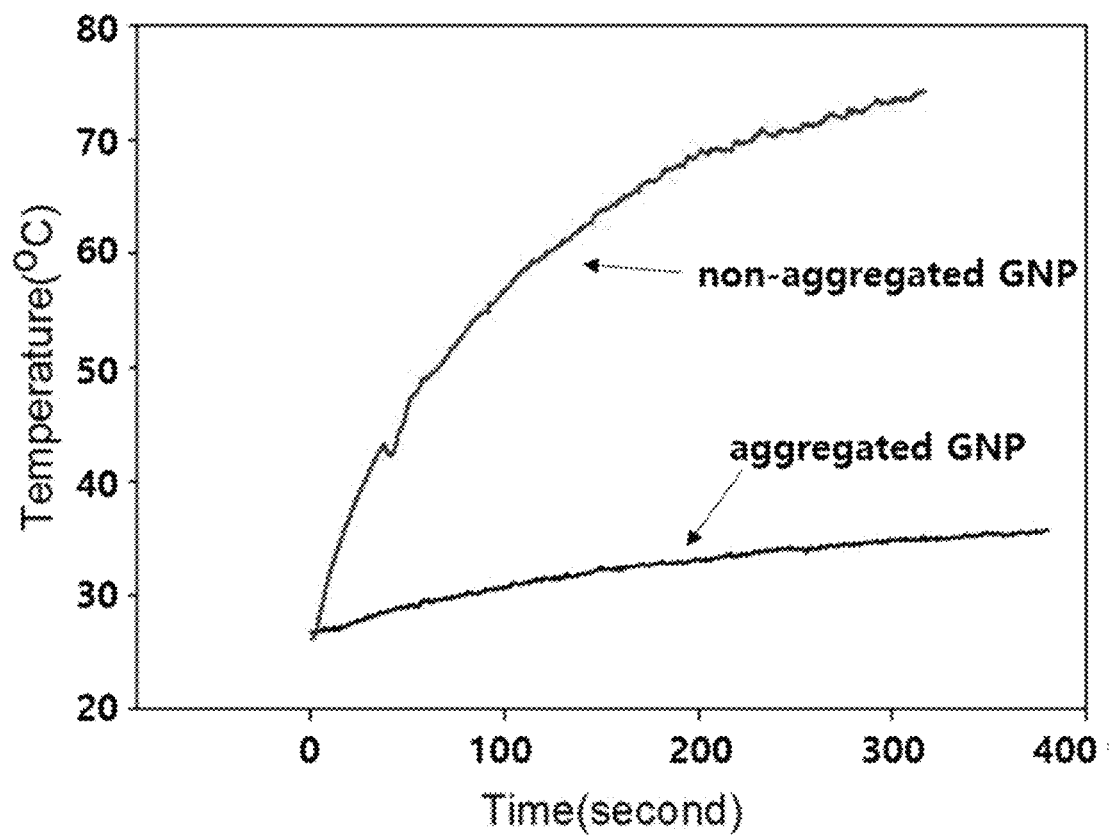
FIG. 12 shows that when the PEG-BR coated gold nanoparticles react with reactive oxygen species, the PEG-BR coating was peeled off, resulting in the aggregation of gold nanoparticles, thereby producing a potent photothermal effect in a near-infrared (NIR) region.

In addition, when the PEG-BR coated gold nanoparticles react with ROS, the PEG-BR coating was peeled off, resulting in the aggregation of gold nanoparticles with a loss of ligands, so that the gold nanoparticles had a potent photothermal effect in an NIR region, leading to a change in absorbance (FIG. 12). This indicates a possibility that a contrast agent based on PEG-BR coated gold nanoparticles can be used not only as a diagnostic tool using CT, but also as a tool for promoting the treatment by photothermal effects in response to ROS in tumors.

Figure 13:
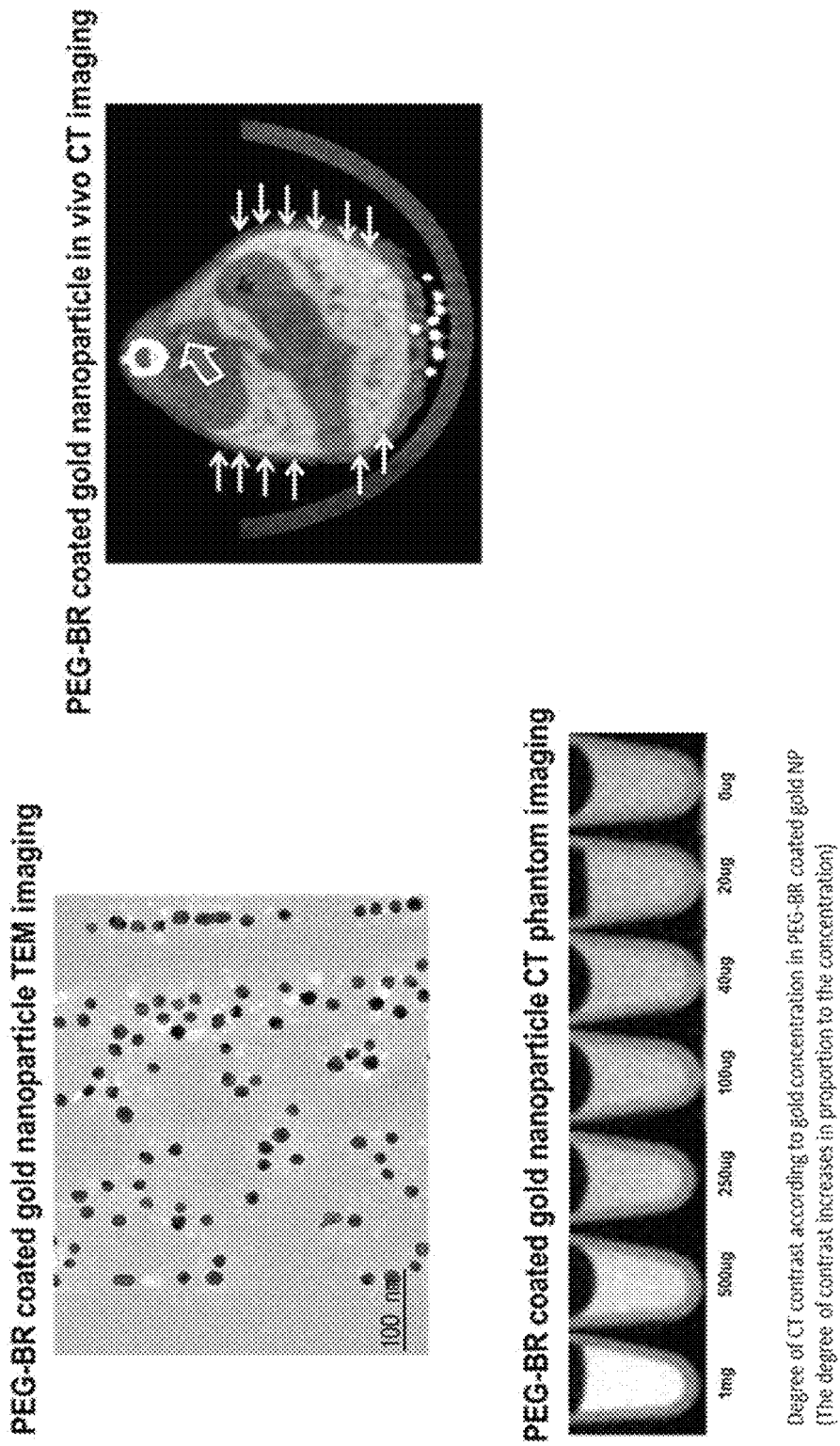
FIG. 13 shows the CT imaging results of mice using PEG-BR coated gold nanoparticles.

In addition, as a result of investigating the CT images of the PEGylated bilirubin coated gold nanoparticles in mice in vivo, it was confirmed that angiography can be performed with long circulation for a long period of time and excellent results were also obtained in imaging major organs, such as liver and spleen (FIG. 13).

Example 5: Preparation of Bilirubin Derivative Particles Containing Metal (Platinum-Based Anticancer Drug) of the Present Invention-3

Figure 14:
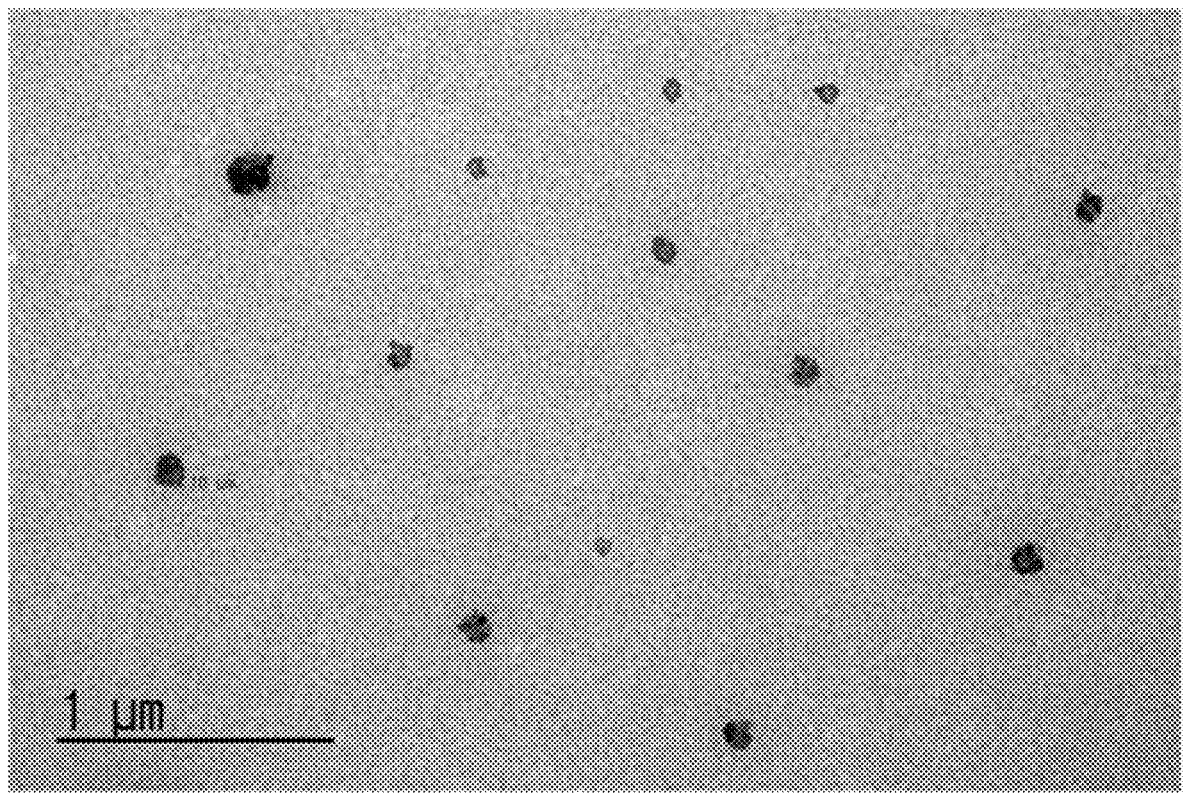
FIG. 14 shows a negatively stained TEM image of cisplatin-loaded bilirubin particles.

In order to validate the chelating effect of forming a complex with a metal and the therapeutic efficacy against a tumor, of the bilirubin derivative particles of the present invention, nanoparticles loading cisplatin, which is the most representative metal drug used for a tumor, were fabricated (FIG. 14). Cisplatin has a platinum metal backbone, and has been used together with a nano-delivery system.

Figure 15:
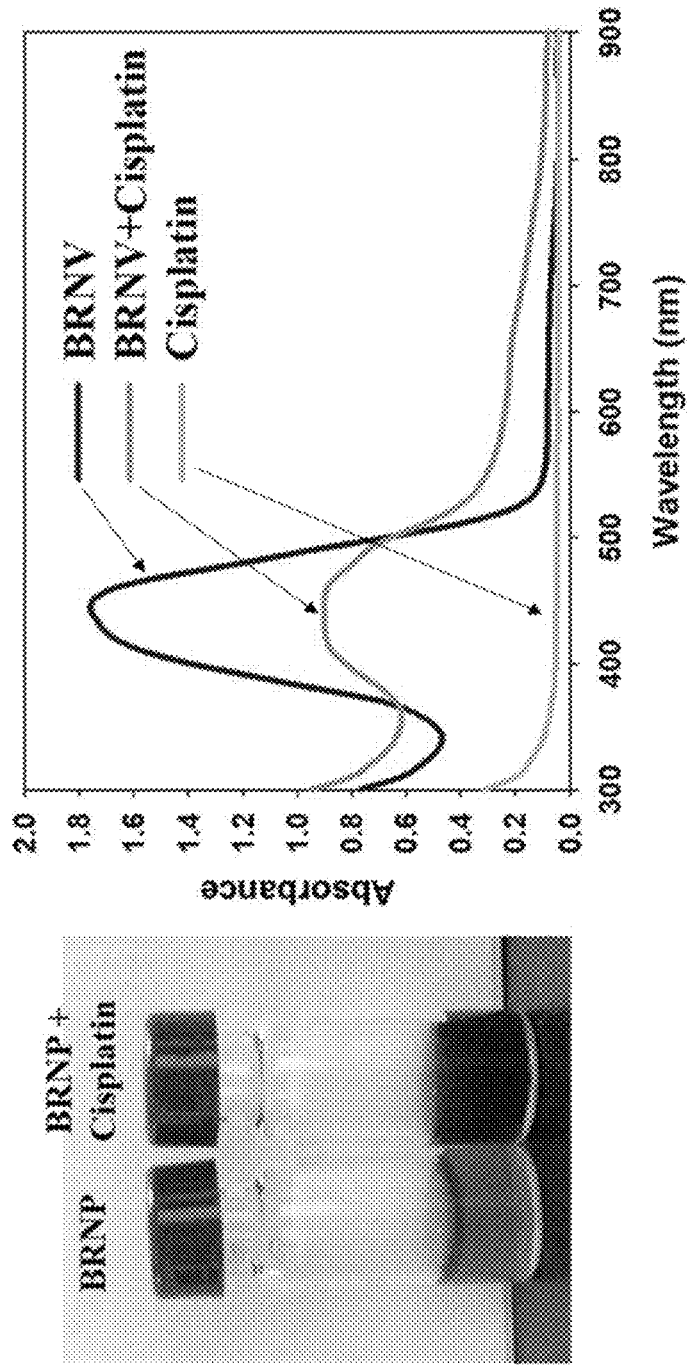
FIG. 15 shows cisplatin chelation and provides an image of suspensions (left side) and a graph of UV/Vis spectra (right side) of general bilirubin particles (BRNP) and bilirubin particles reacting with cisplatin (BRNP+Cisplatin).
Figure 16:
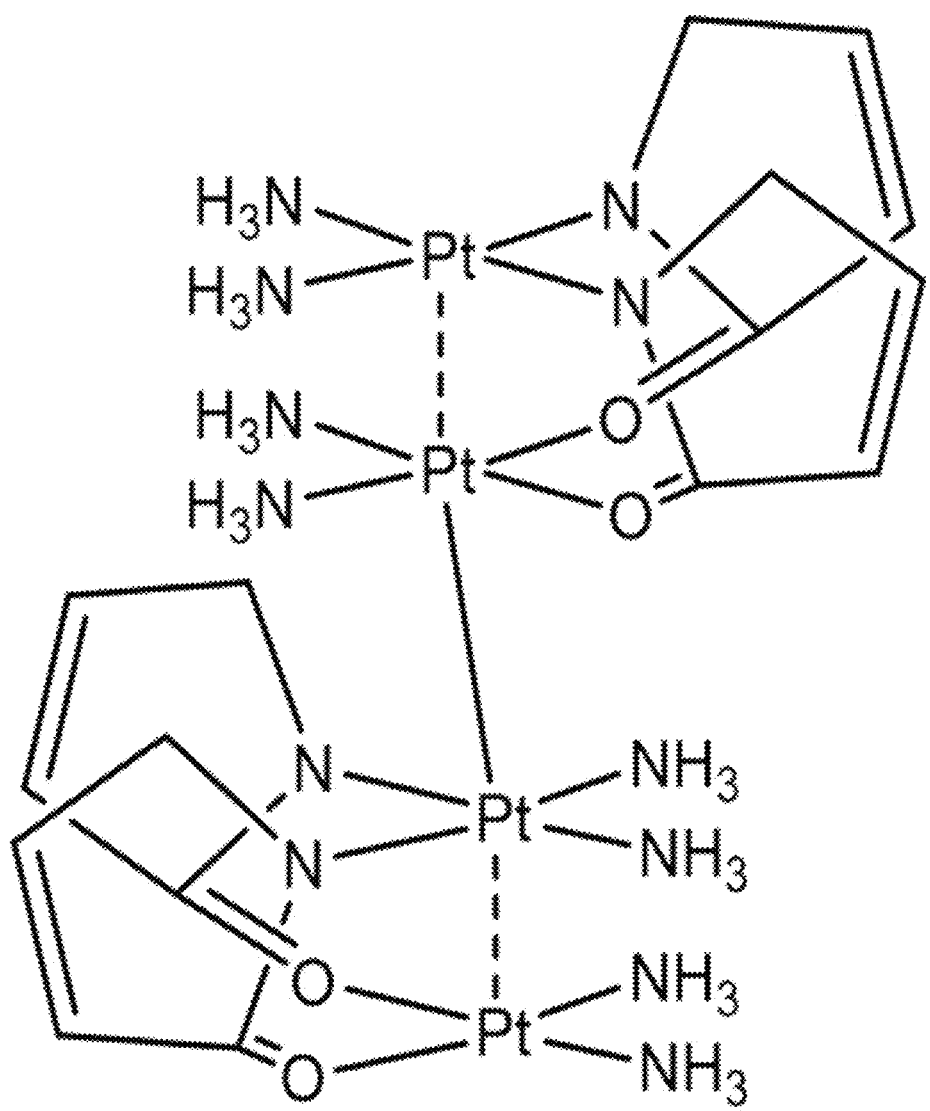
FIG. 16 shows an estimated reaction mechanism of a PEG-bilirubin particle and cisplatin.

As a result of reaction of PEGylated bilirubin (PEG-BR) particles and a hydrolysis product of cisplatin, it was confirmed that cisplatin was loaded with an unprecedented color change in the solution (FIG. 15). A schematic diagram showing the binding principle between the PEGylated bilirubin and cisplatin is shown in FIG. 16.

Figure 17A:
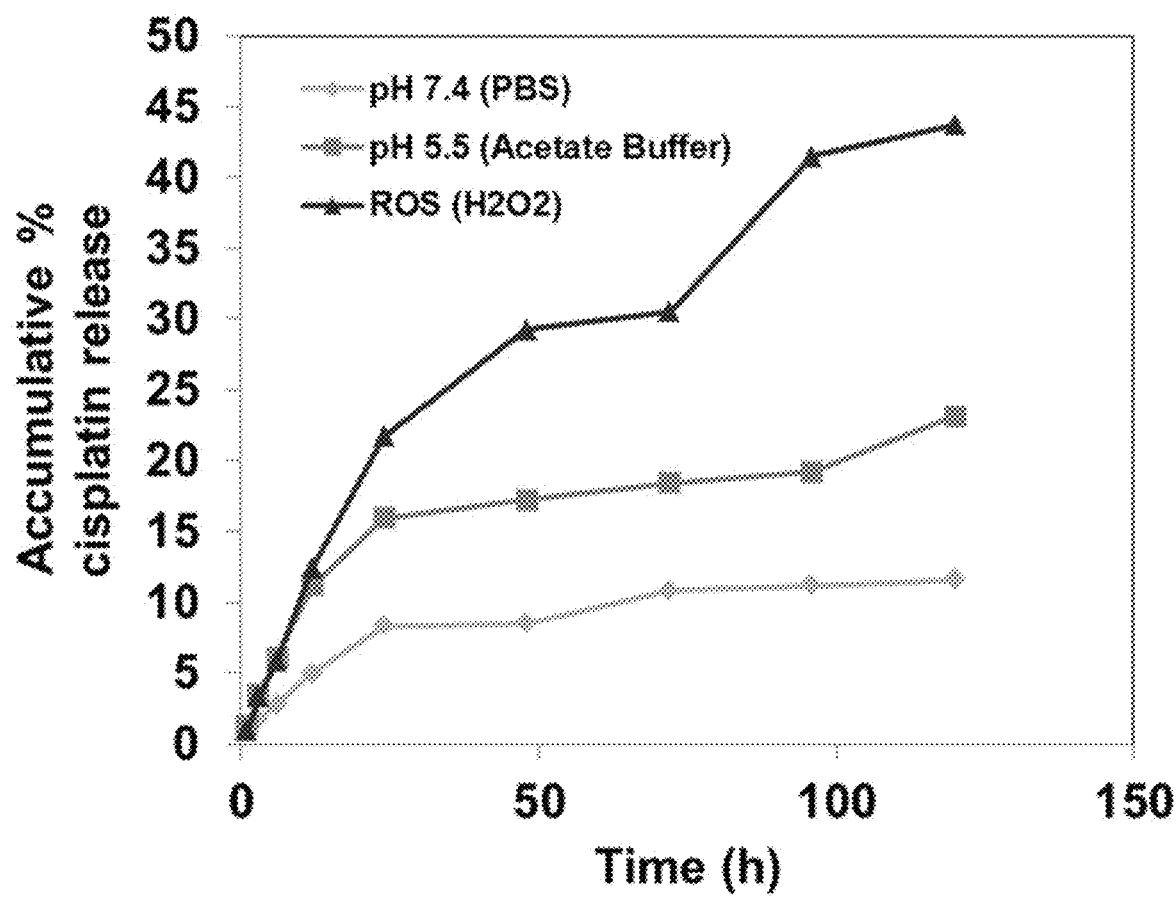
FIG. 17a and FIG. 17b show cisplatin release patterns according to several conditions (pH and ROS) and time in cisplatin-encapsulated PEG-bilirubin particles.
Figure 17B:
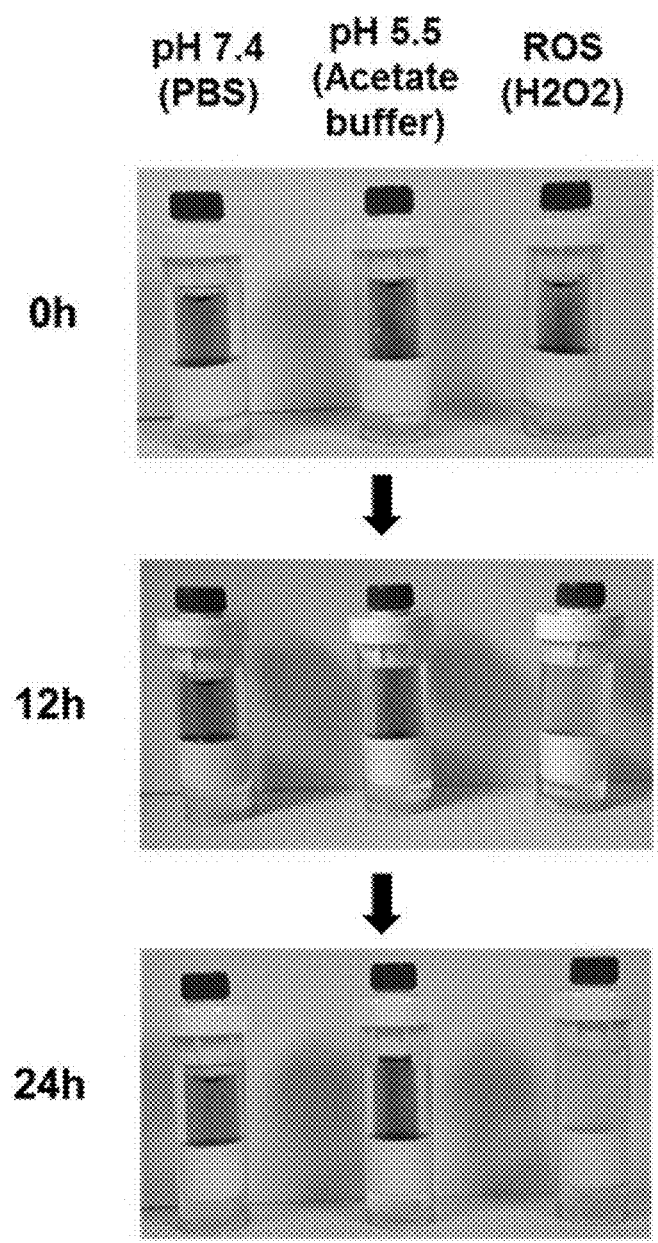

In addition, as a result of conducting a cisplatin release test according to several conditions (pH and ROS) and time in cisplatin-encapsulated bilirubin nanoparticles, cisplatin showed the highest release rate in response to ROS, to show the highest release proportion, followed by a high release rate at acidic conditions (pH 5.5), which was known to be similar to environment of intracellular lysosomes, and the lowest release at physiological pH (FIGS. 17a and 17b).

The above results indirectly confirmed that the bilirubin derivative particle containing a metal of the present invention can stably encapsulate cisplatin as a platinum-based drug therein and selectively release the encapsulated drug to the surrounding micro-environment.

Example 6: Photo-Acoustic and Photothermal Activities of Bilirubin Derivative Particles Containing Metal (Platinum-Based Anticancer Drug) of the Present Invention In the sacrifice of the decreased Soret band peak, the increase in absorbance at the IR region (red shift) induces remarkable photothermal activity at a light of 808 nm. Since the bilirubin nanoparticle per se has remarkable IR light sensitivity, the photothermal activity could not be derived from an original general IR light source. Such a change and newly acquired photon characteristics can be explained by the "Platinum Blues" theory. According to the theory, the hydrolysis product of cisplatin can be obtained from the reaction with an amide ligand.

As for the nanoparticles of the present invention in which PEGylated bilirubin is coordinated to cisplatin, the present inventors used such a metal-coordination complex for photo-acoustic imaging and photo-thermal therapy (PTT) due to the newly obtained absorbance in the near infrared region (NIR region). The photo-acoustic imaging and photothermal therapy share the same principle in light of a particular wavelength.

Figure 18:
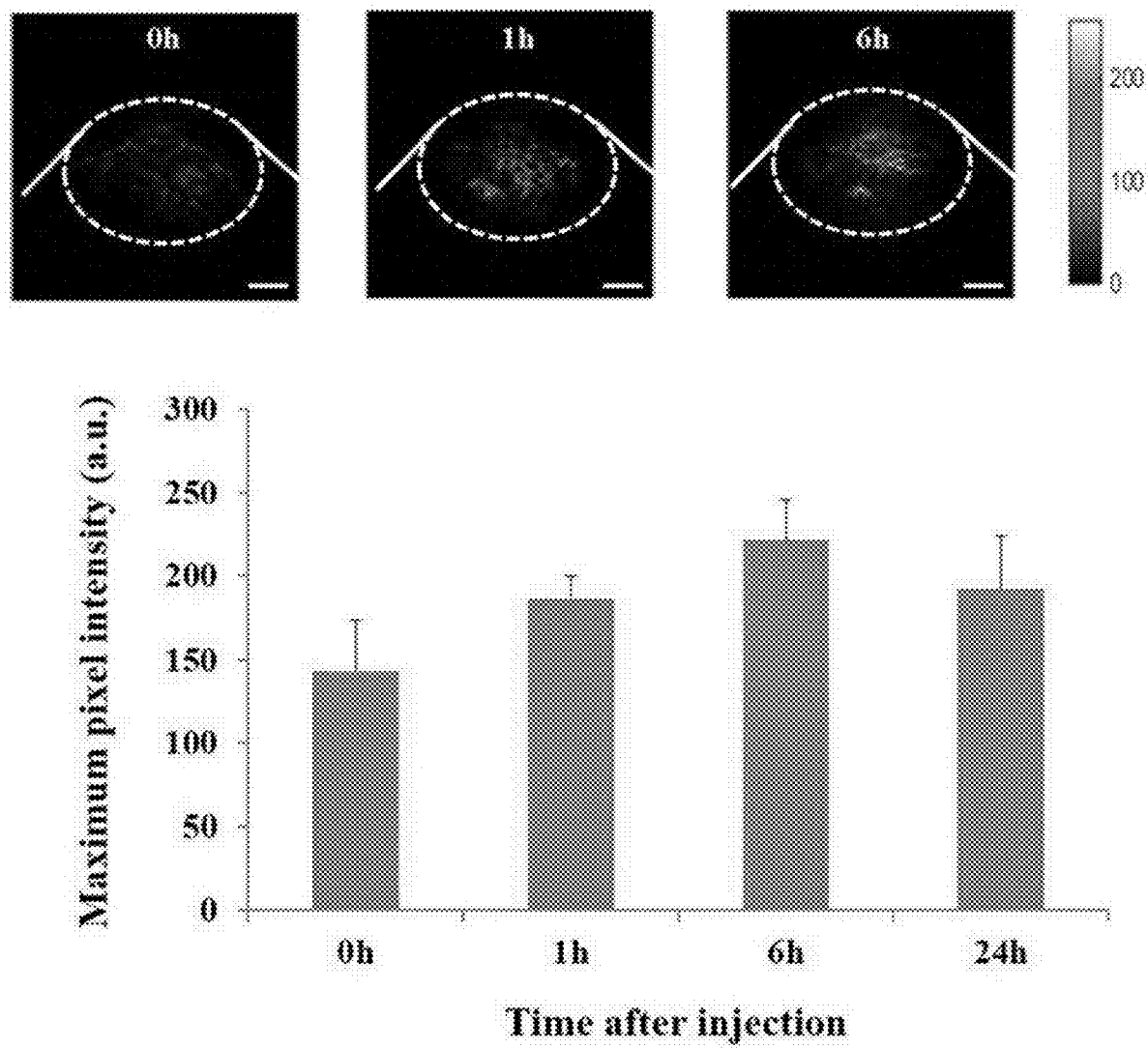
FIG. 18 shows in vivo photo-acoustic images over time after injection into xenograft tumor of a nude mouse and semi-quantitative analysis of pixel values in the tumor corresponding thereto.
Figure 19:
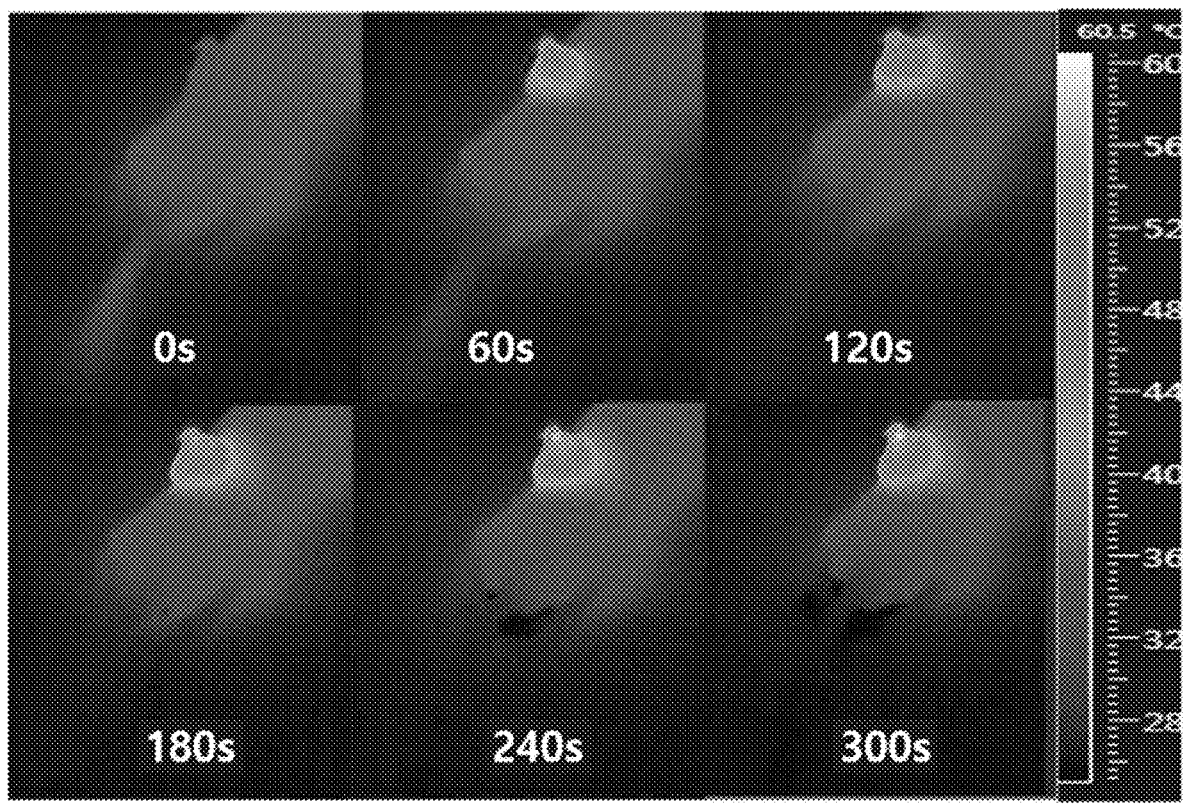
FIG. 19 shows infrared thermal images at different time intervals of a tumor xenograft mouse exposed to a near infrared (NIR) laser at an output power of 800 mW/cm$^2$.
Figure 20:
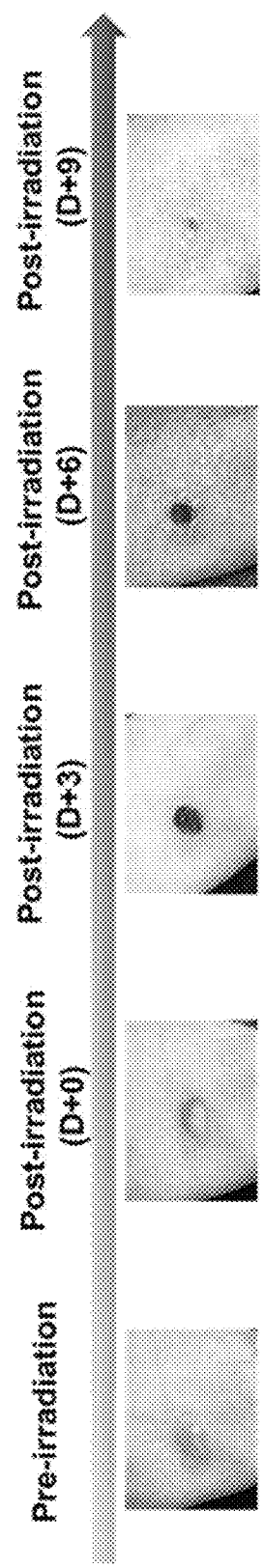
FIG. 20 and FIG. 21 show the results of observation according to the period when cisplatin-encapsulated PEG-bilirubin particles were injected into a xenograft tumor of a nude mouse and then a photothermal therapy was performed on the nude mouse using light.
Figure 21:
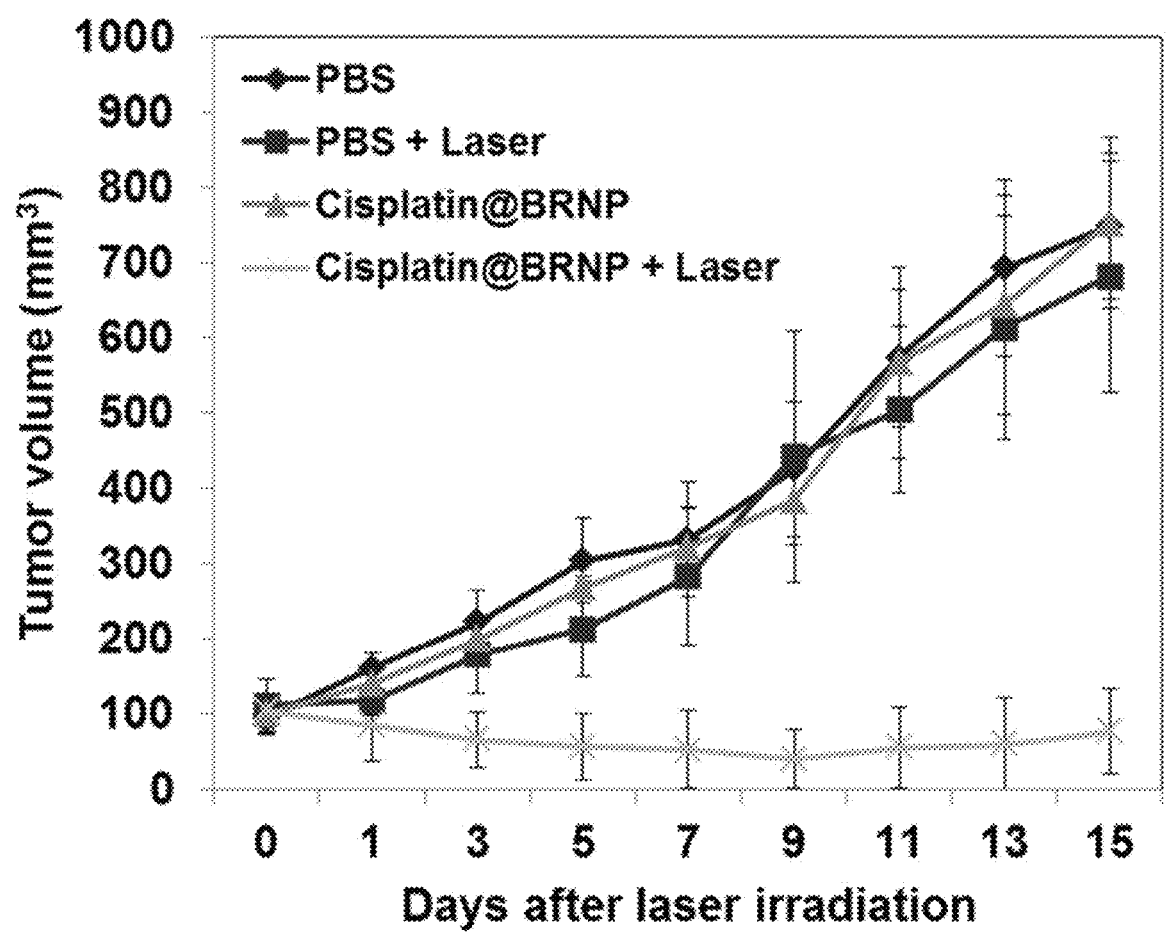

Upon application to in vivo photo-acoustical imaging in tumor xenograft model mice, it was confirmed that the photo-acoustic signal was gradually increased after the intravenous injection of the bilirubin derivative of the present invention (FIG. 18). Therefore, the possibility of photo-thermal therapy was confirmed in the same conditions, and the surface temperature of a tumor was rapidly increased to 55-60° C. within 5 minutes after exposure to light of 808 nm (FIG. 19). Resultingly, a significant tumor volume reduction effect over time was observed in the group subjected to photo-thermal therapy using actual light (FIGS. 20 and 21).

Example 7: ROS-Responsiveness of Bilirubin Derivative Particles Containing Metal of the Present Invention 7-1. Confirmation of ROS-Responsiveness of Bilirubin Derivative Particles Containing Iron Nanoparticles (Visible Color Change)

In order to investigate ROS-responsiveness of the bilirubin derivative particles of the present invention and a change thereof, the change of PEGylated bilirubin coated iron nanoparticles of the present invention according to the concentration of ROS was examined.

First, a suspension containing PEGylated bilirubin coated iron nanoparticles was prepared by the same method as in the above-described example, and NaOCl (100, 10, 1, 0.1, 0 mM) and AAPH* (100, 10, 1, 0.1, 0 mM), and hydrogen peroxide water (100 mM) were added according to the concentration, and the results were observed with the naked eye and by an optical microscope. [*2,2'-Azobis(2-am idinopropane) dihydrochloride (AAPH)]. In addition, PEGylated DSPE coated iron nanoparticles as a negative control were used. [1,2-Distearoyl-sn-glycero-3-phosphoethanolamine (DSPE)]

The results are shown in FIGS. 22 to 25.

Figure 22:
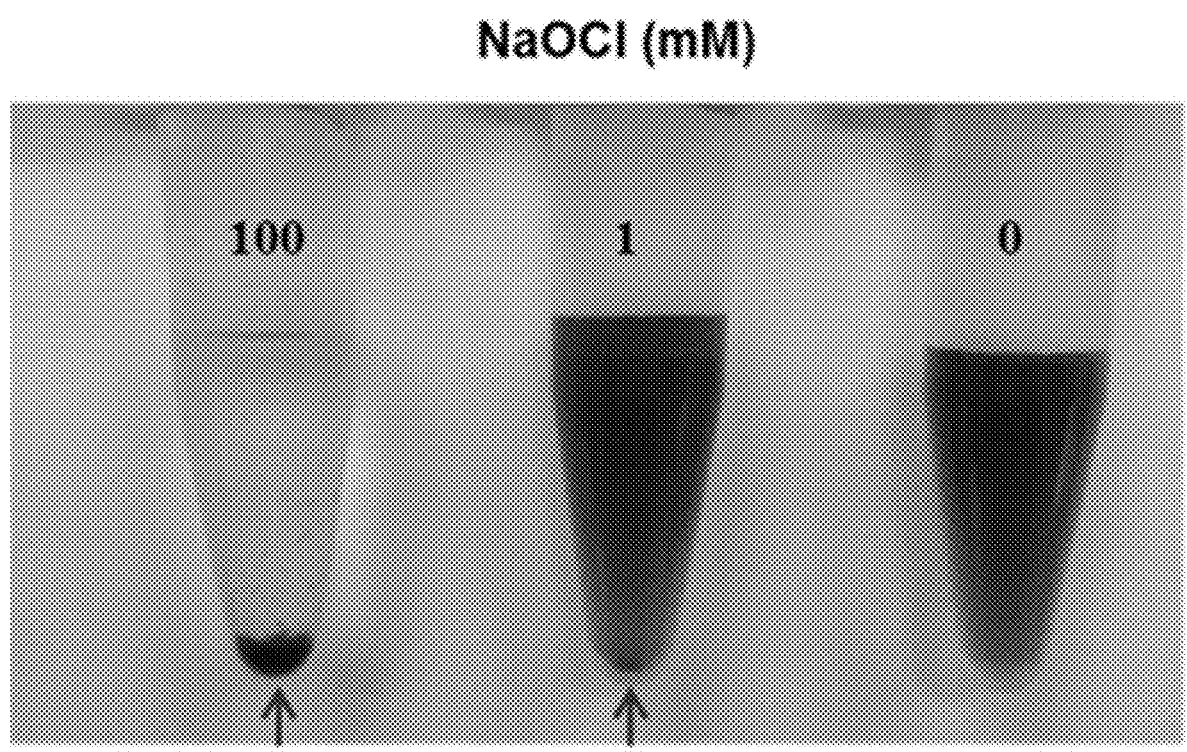
FIG. 22 shows the change of an aqueous solution of PEGylated bilirubin coated iron nanoparticles of the present invention according to the concentration of reactive oxygen species.

As shown in FIG. 22, at a concentration of NaOCl of 100 mM, all the PEGylated bilirubin, which has coated the iron nanoparticles, were dropped due to a high concentration of ROS, and thus the remaining hydrophobic iron nanoparticles aggregate each other and settled down. As a result, the inherent color of the iron nanoparticle aqueous solution seen in the right two tubes was also lost, thus giving a clear water color. Whereas only a very small amount aggregated (red arrow) in the middle tube group treated with 1 mM as an intermediate concentration, and showed a darker coffee color due to weaker aggregation of iron nanoparticles compared with a control group (1 mM) on the right side.

Figure 23:
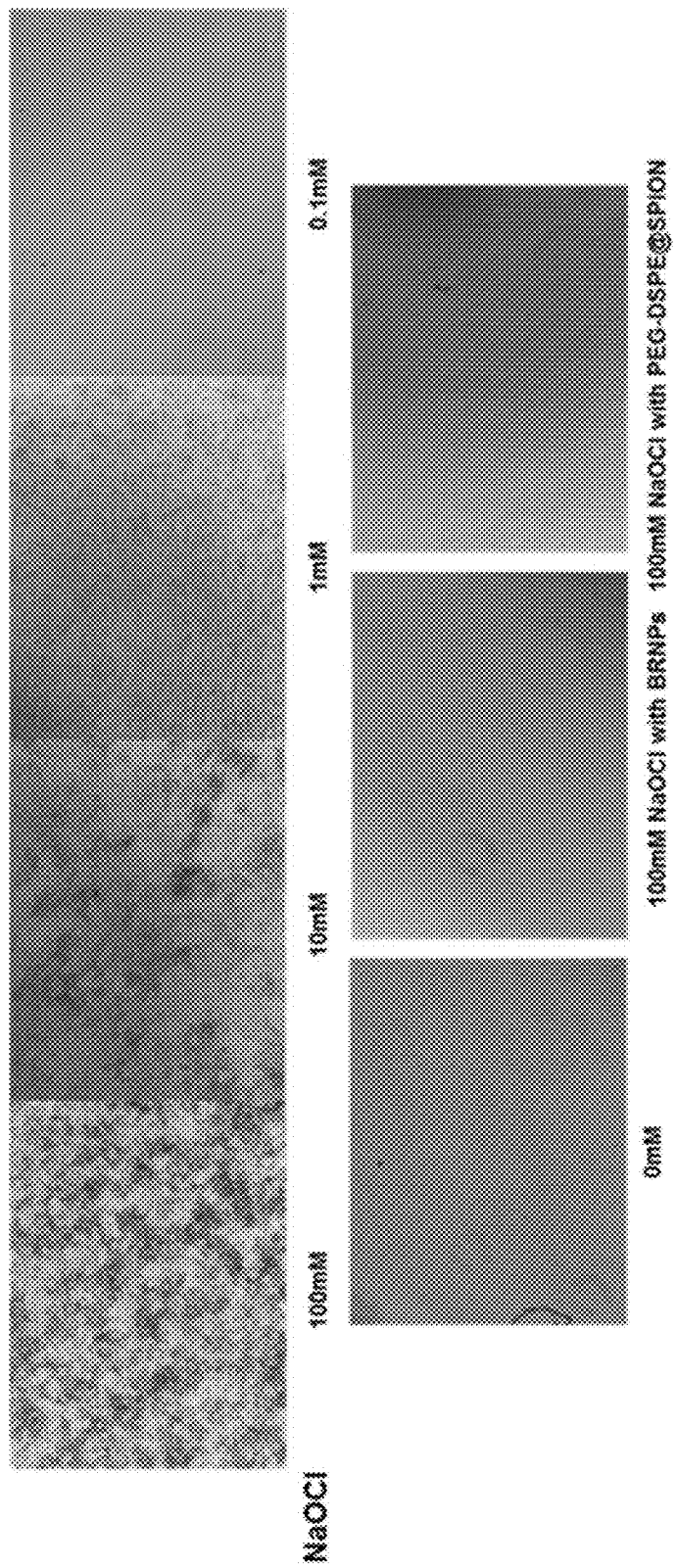
FIG. 23 shows the change of an aqueous solution of PEGylated bilirubin-coated iron nanoparticles of the present invention according to the concentration of NaOCl as reactive oxygen species.
Figure 24:
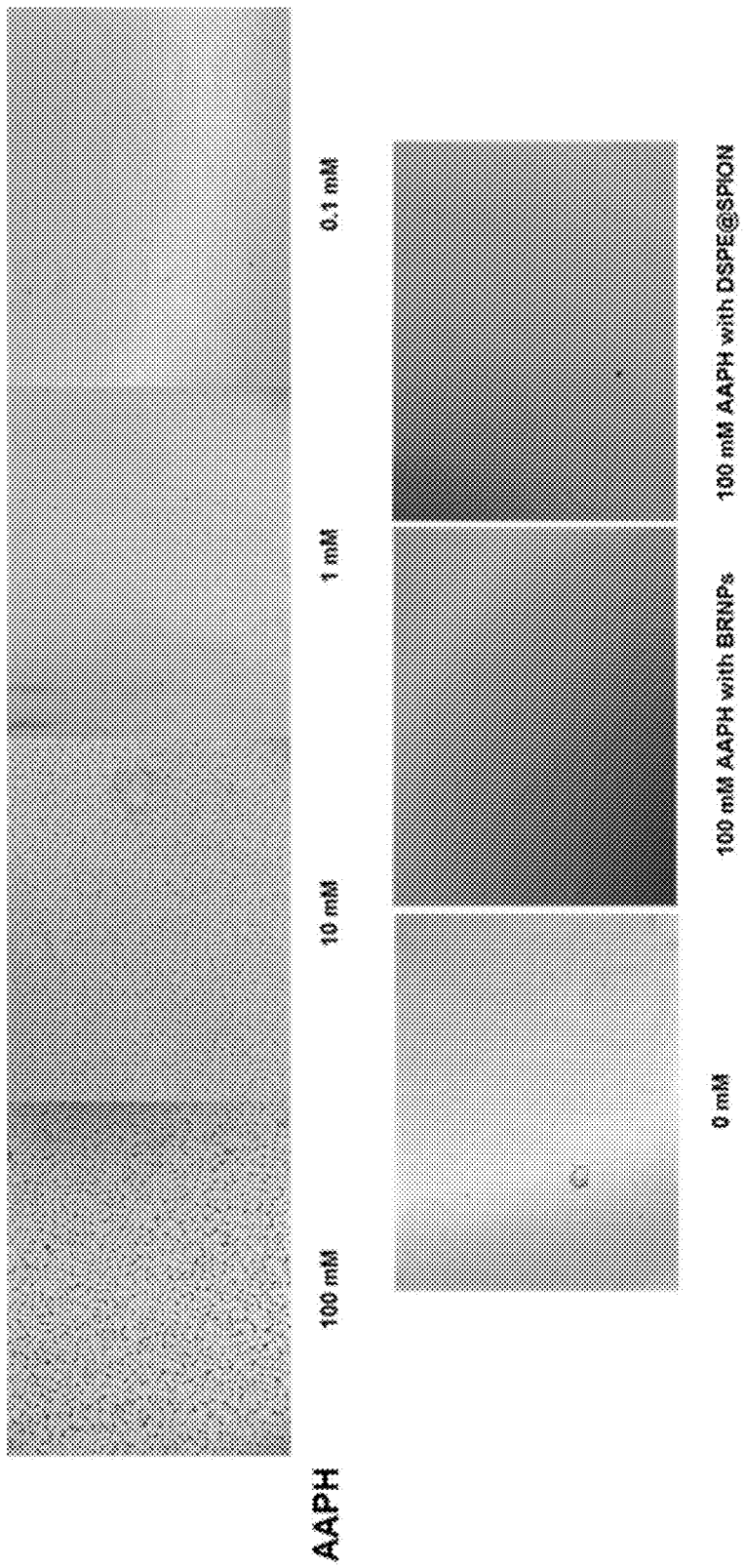
FIG. 24 shows the change of an aqueous solution of PEGylated bilirubin coated iron nanoparticles of the present invention according to the concentration of 2,2'-azobis(2-amidinopropane) dihydrochloride (AAPH) as reactive oxygen species.
Figure 25:
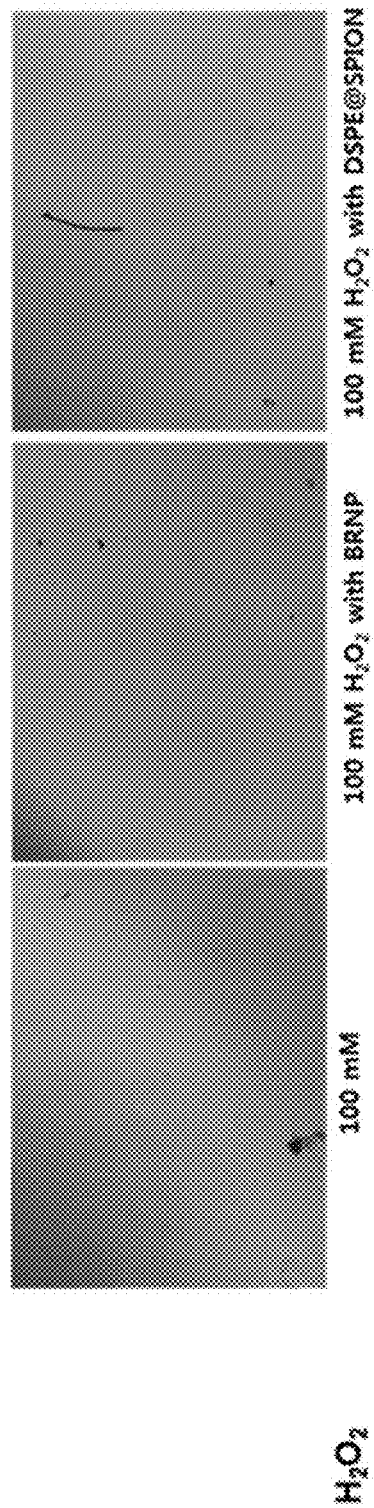
FIG. 25 shows the change of an aqueous solution of PEGylated bilirubin coated iron nanoparticles of the present invention according to the concentration of hydrogen peroxide water as reactive oxygen species.

As shown in FIGS. 23 to 25, it was confirmed that the ROS-responsiveness was different in the order of hypochlorite (HOCl)>>AAPH>>>>>hydrogen peroxide water. It was also confirmed that PEGylated 1,2-distearoyl-sn-glycero-3-phosphoethanolamine (DSPE) coated iron nanoparticles, used as a negative control, did not react with any of three types of ROS. Therefore, it could be confirmed that the reaction of the ROS and the PEGylated bilirubin coated iron nanoparticles was very specific.

7-2. Confirmation of ROS-Responsiveness of Bilirubin Derivative Particles Containing Gold Nanoparticle (Absorbance Change)

In order to quantitatively investigate ROS-responsiveness of the bilirubin derivative particles of the present invention, the absorbance before and after the reaction of the bilirubin derivative particles and ROS was measured. Specifically, the change of the solution before and after the reaction of PEGylated bilirubin coated gold nanoparticles with each type of ROS was measured using naked eyes and absorbance.

Figure 26:
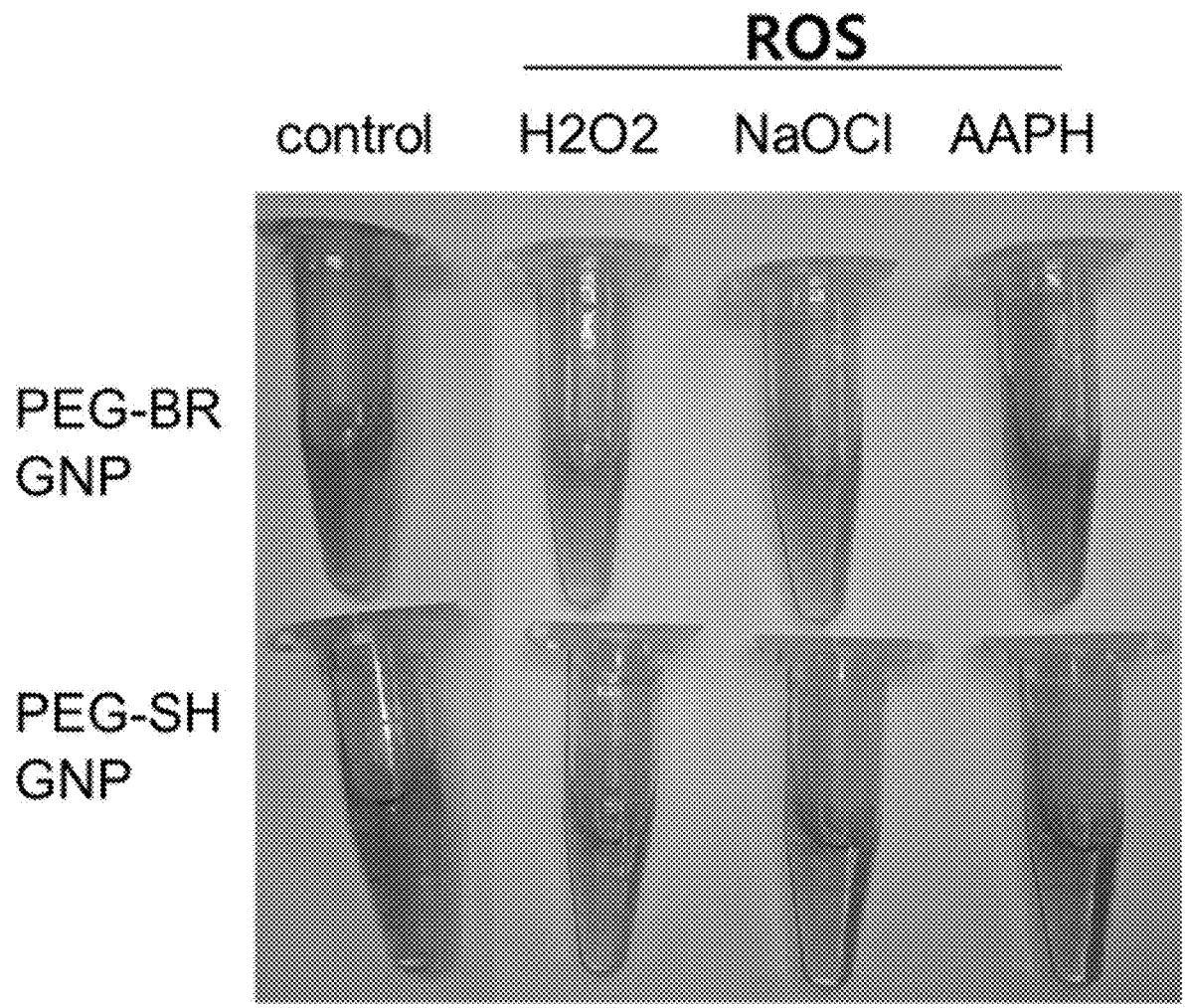
FIG. 26 shows the visible changes of the aqueous solution of PEGylated bilirubin-coated gold nanoparticles (PEG-BR GNP) of the present invention before and after reaction with respective types of reactive oxygen species ($H_2O_2$, NaOCl, and AAPH).
Figure 27:
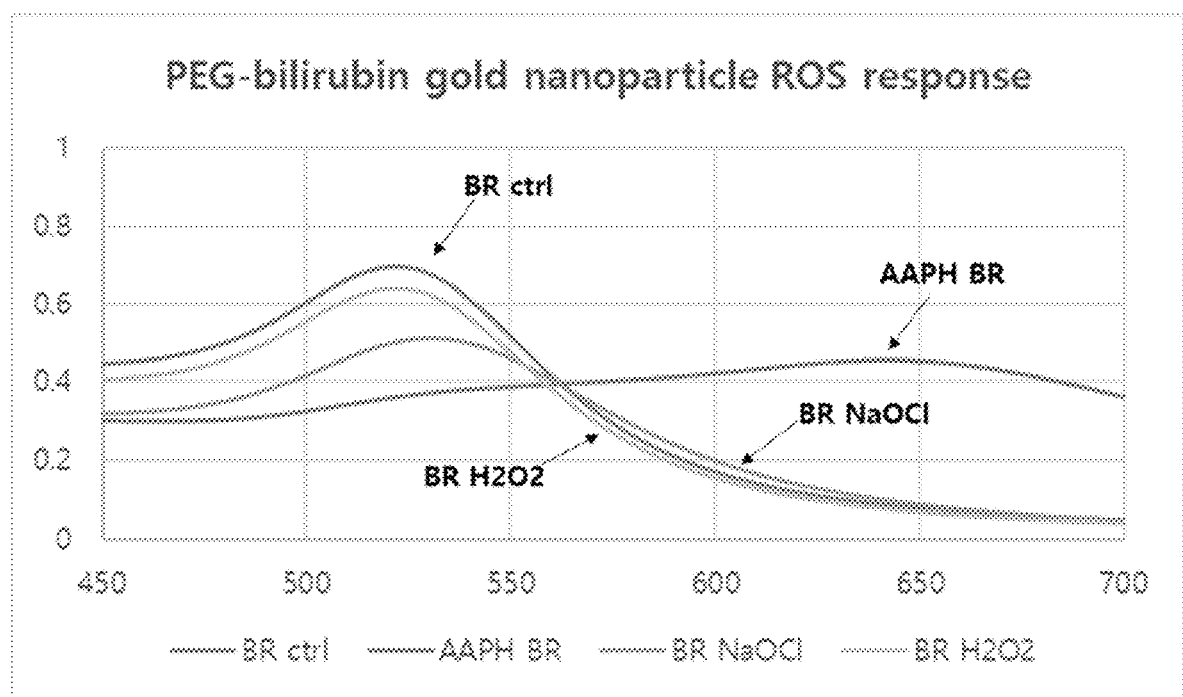
FIG. 27 shows the absorbance changes of the aqueous solution of PEGylated bilirubin coated gold nanoparticles (PEG-bilirubin gold nanoparticle) of the present invention before and after reaction with respective types of reactive oxygen species ($H_2O_2$, NaOCl, AAPH).
Figure 28:
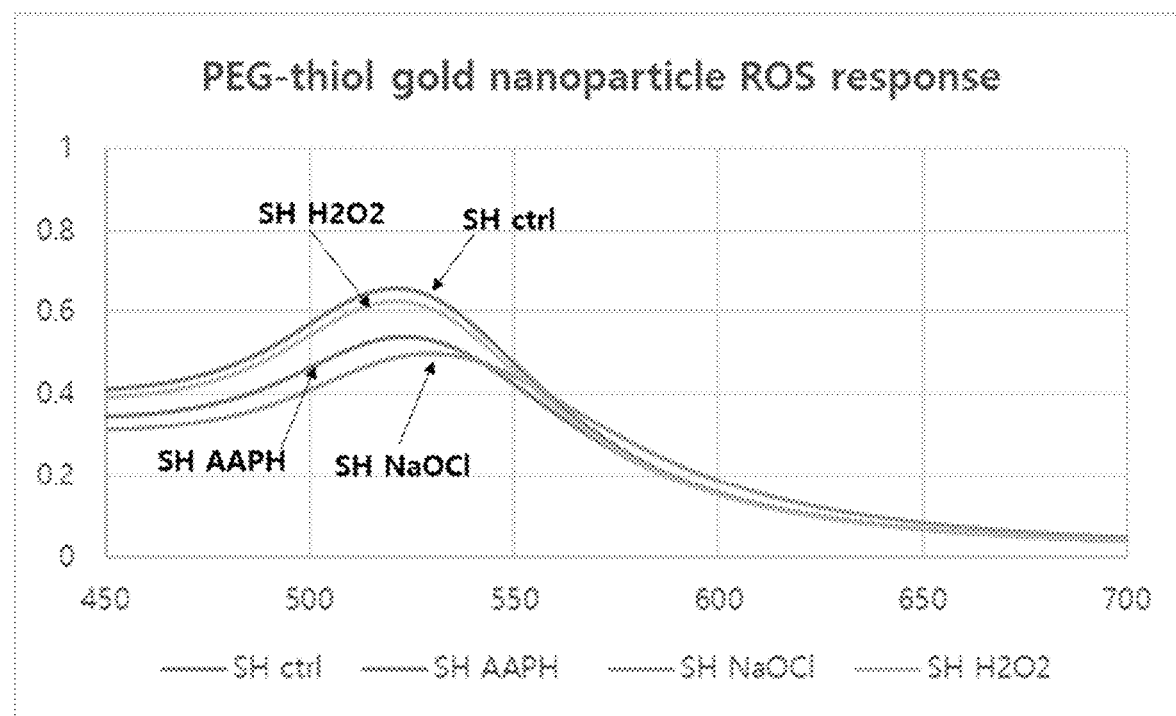
FIG. 28 shows the absorbance changes of the aqueous solution of PEG-thiol coated gold nanoparticles, as a control group for the PEGylated bilirubin of the present invention, before and after reaction with respective types of reactive oxygen species ($H_2O_2$, NaOCl, and AAPH).

The results are shown in FIGS. 26 and 28.

As for AAPH, only PEGylated bilirubin coated gold nanoparticles specifically reacted with AAPH, and PEGylated thiol (PEG-SH) coated gold nanoparticles, used as a negative control, did not react with AAPH. As for hypochlorite (HOCl), both of PEGylated bilirubin coated gold nanoparticles and PEGylated thiol (PEG-SH) coated gold nanoparticles were observed to react with hypochlorite, and thus it was confirmed that the bilirubin derivative particles of the present invention showed higher response specifically to ROS (AAPH).

It could be seen from the above results that the bilirubin derivative particles of the present invention can be favorably used in determining the type and concentration of ROS.

Figure 29:
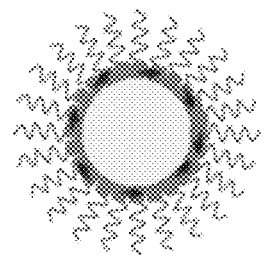
FIG. 29 is a schematic diagram of a bilirubin derivative particle prepared by the manganese ion ($Mn^{2+}$) coordination.
Figure 29:
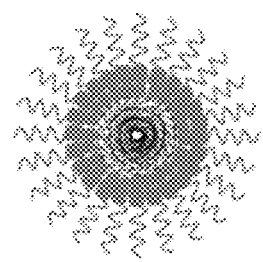
Figure 30:
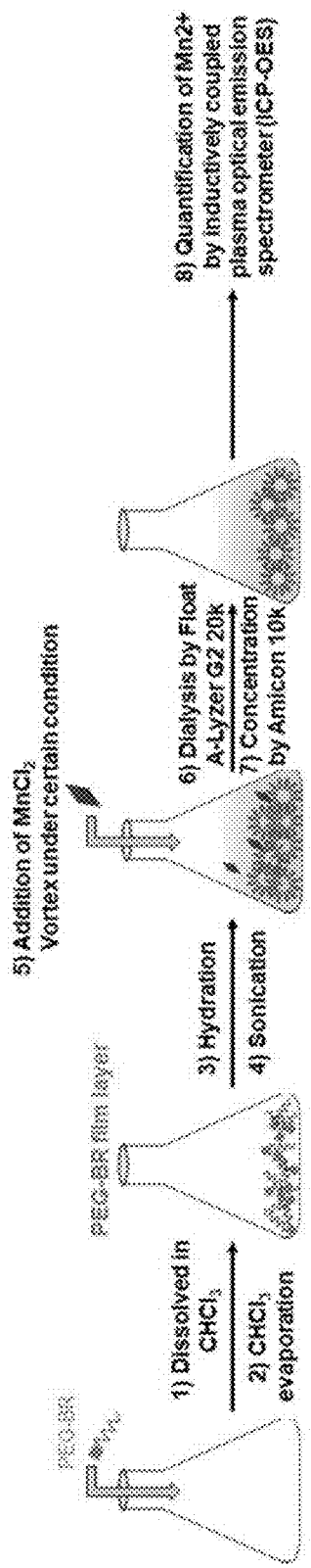
FIG. 30 shows a preparation process for bilirubin derivative nanoparticles coordinating manganese ion ($Mn^{2+}$) as a paramagnetic element for use in MRI imaging. PEG-bilirubin is used to form nanoparticles, which are then mixed with manganese ions, to thereby producing manganese ion-coordinated particles.

Example 8: ROS-Responsiveness of Manganese Ion-Coordinated Bilirubin Derivative Particles of the Present Invention 8-1. Preparation of Manganese Ion-Coordinated Bilirubin Derivative Particles In order to further investigate the ROS-responsive and change of the bilirubin derivative particles containing a metal of the present invention, bilirubin derivative particles were prepared by the manganese ion ($Mn^{2+}$) coordination. A schematic diagram and a preparation method of the manganese ion-coordinated bilirubin derivative particles are shown in FIGS. 29 and 30. Specifically, a $MnCl_2$ aqueous solution was dropped using a syringe pump such that the molar ratio of PEG-BR:$MnCl_2$ was 1:1 while strongly mixing an aqueous solution of the bilirubin derivative (PEG-BR) particles prepared in example 1 above (step 5)). Thereafter, a reaction was performed at 37° C. for 48 hours. After the reaction was completed, the manganese ions not bound with the bilirubin nanoparticles were removed by using a dialysis bag (float A-Lyzer, MW cutoff: 20K) (step 6)), followed by concentration using Amicon 10K (step 7)), thereby preparing manganese ion-coordinated bilirubin derivative nanoparticles. In order to measure the amount of manganese ions bound to the prepared bilirubin derivative nanoparticles, ICP-OES (Agilent ICP-OES 5110) was used (step 8)). As a result, it was confirmed that 22.67±2.20 mg/kg (based on PEG-BR 1 mM) of manganese ions were bound in the manganese ion-coordinated bilirubin derivative nanoparticles of the present invention.

8-2. Confirmation of ROS-Responsiveness of Manganese Ion-Coordinated Bilirubin Derivative Particles (Ion Concentration, TEM Imaging, and MR Imaging)

Figure 31:
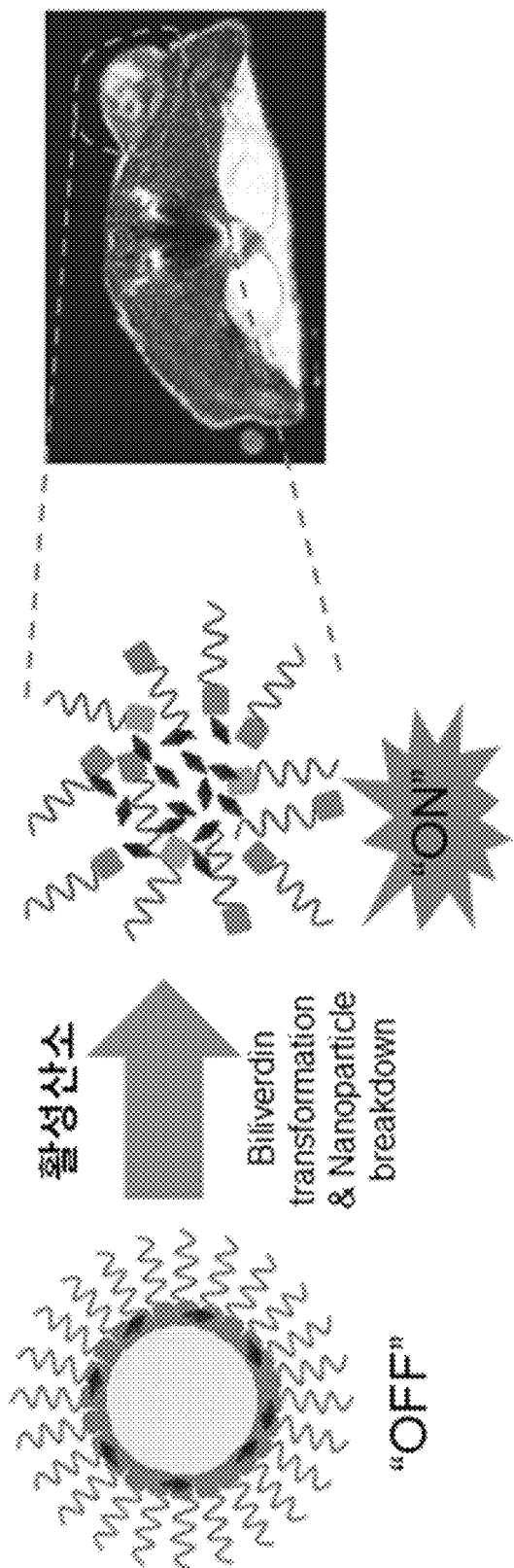
FIG. 31 is a schematic diagram showing that the particles containing a bilirubin derivative and a metal, of the present invention, can detect or diagnose reactive oxygen species. Specifically, when the manganese ion-coordinated bilirubin derivative reacts with reactive oxygen species, hydrophobic bilirubin was transformed into hydrophilic biliverdin or degraded into bilirubin fragments, leading to weakened binding and nanoparticle breakdown. As a result, the coordinated manganese ions were separated, leading to MRI image enhancement.

In order to investigate the reaction of the manganese ion-coordinated bilirubin derivative particles of the present invention, prepared in example 8-1, with ROS, hypochlorite was added to the manganese ion-coordinated bilirubin derivate particles to obtain the release amount of manganese ions and MRI T1 weighted images therefor. FIG. 31 illustrates that when the manganese ion-coordinated bilirubin derivative of the present invention reacted with ROS, the hydrophilic bilirubin was transformed into hydrophilic biliverdin, leading to weaken binding and nanoparticle breakdown, and as a result, the coordinated manganese ions were separated, and thus the ROS were imaged using MRI.

Specifically, 1 ml of the manganese ion-coordinated bilirubin nanoparticles were added into a dialysis bag (Float A-Lyzer, MW cutoff: 20K), and 1 mM NaOCl was added to 99 ml of distilled water, and then the dialysis of manganese ions separated from the coordination state was carried out at room temperature with shaking. At predetermined times (0, 1, 2, 3, 6, 12, 24, 48 and 72 hr), 50 ul of fractions were collected from the inside of the dialysis bag, and the amount of manganese contained in each fraction was determined through ICP-MS (Agilent ICP-MS 7700S).

Figure 32:
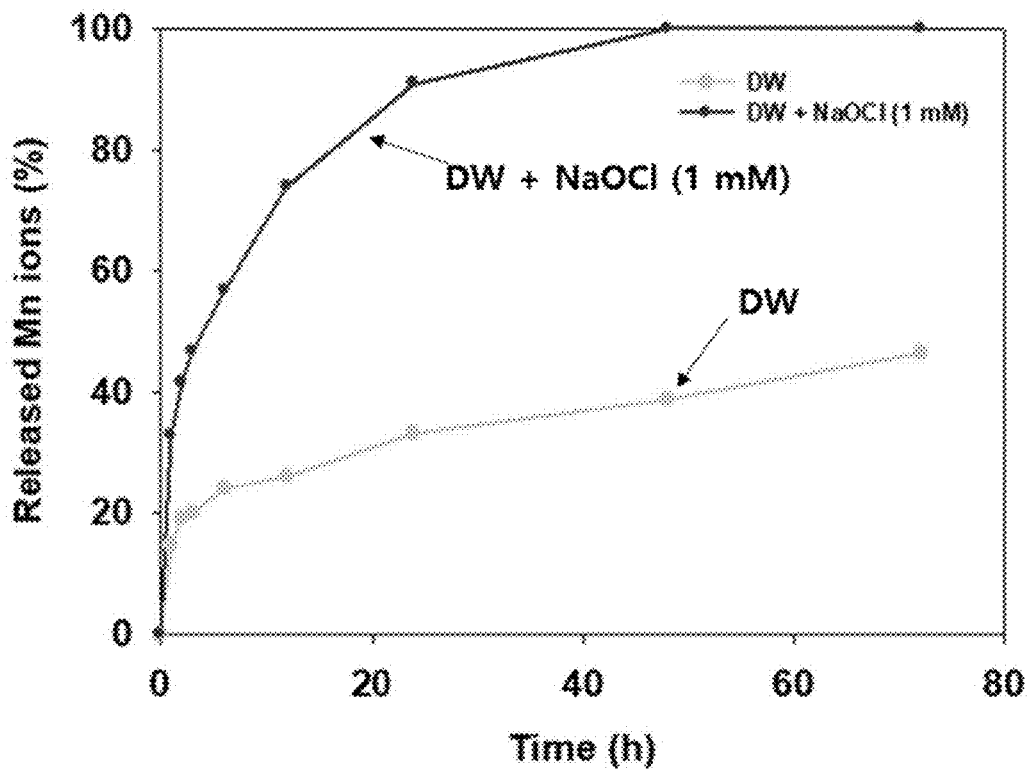
FIG. 32 shows a pattern in which the manganese ion-coordinated bilirubin derivative particles release manganese ions by the stimulation of reactive oxygen species.

The results are shown FIG. 32. As shown in FIG. 32, the manganese ion-coordinated bilirubin derivative particles of the present invention released manganese ions by ROS stimulation.

Figure 33:
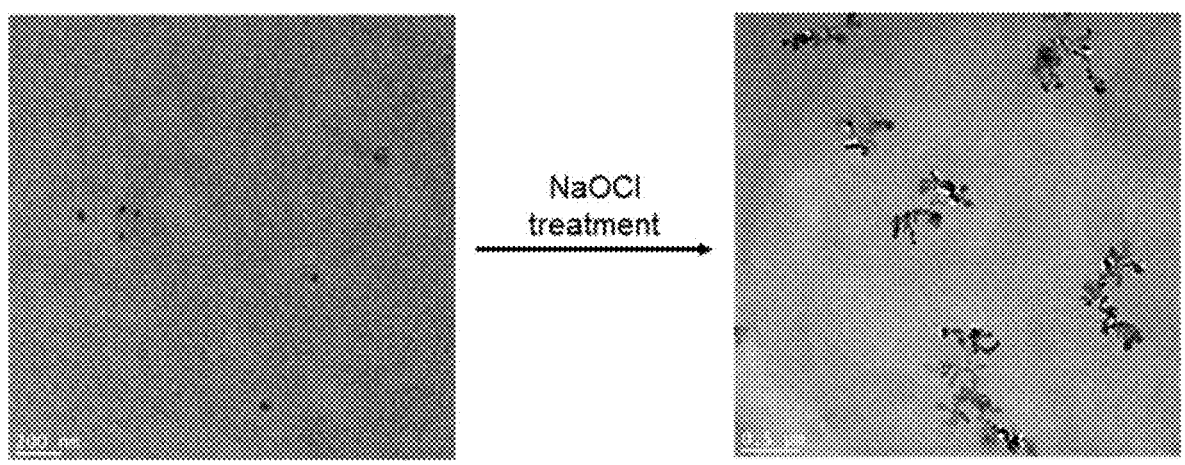
FIG. 33 shows TEM images before and after the manganese ion-coordinated bilirubin derivative (PEG-BR) nanoparticles were treated with hypochlorite as a reactive oxygen generator.

The present inventors also observed, through a transmission electron microscope, the morphological changes of the manganese ion-coordinated bilirubin derivative (PEG-BR) nanoparticles of the present invention before and after the treatment with hypochlorite. The results are shown FIG. 33. As shown in FIG. 33, it could be confirmed that the manganese ion-coordinated bilirubin derivative particles gathered together at one place to form a small sphere before the stimulation of ROS (hypochlorite), but after the stimulation, the particles did not gather but are dispersed since the binding of manganese ion and bilirubin was transformed.

The present inventors also observed MR image signal intensity changes of the manganese ion-coordinated bilirubin derivative (PEG-BR) nanoparticles of the present invention before and after the treatment with hypochlorite. A 3-Tesla MRS 3000 scanner (w/a birdcage rat head coil, MR Solutions, Surrey, United Kingdom) with a 17-cm bore size was used as a measuring instrument, and the measurement parameters of the horizontal T1-weighted images were as follows:

Time of repetition (TR)/echo time (TE); 550 ms/11 ms, flip angle; 90°, field of view (FOV); 45 mm×45 mm, slice thickness; 1.5 mm, matrix number; 256×128.

Figure 1:
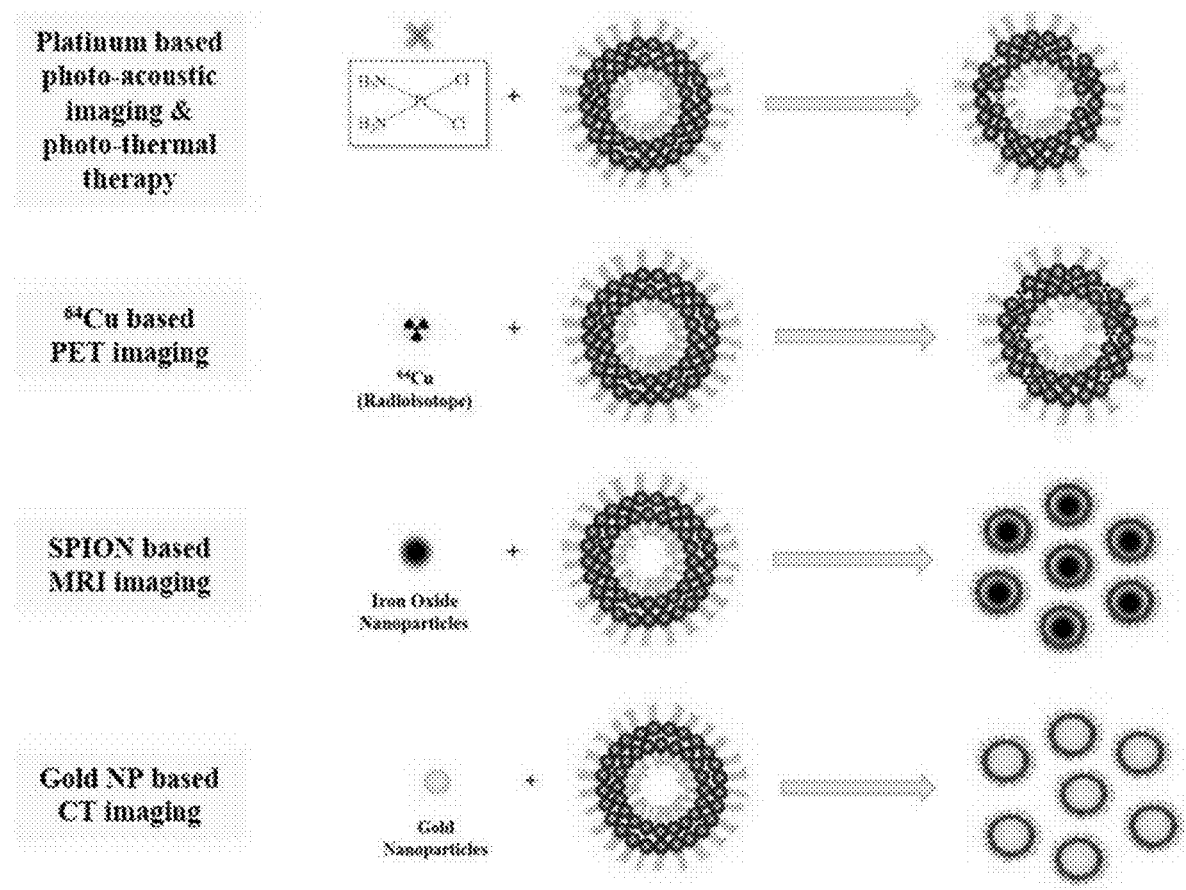
FIG. 1 shows examples of application using bilirubin derivative particles of the present invention.

The results are shown in FIG. 1 and table 1.

TABLE 1

| | Signal-to-noise ratio (T/N contrast ratio) = (mean signal intensity)/{(standard deviation of noise intensity) * 100} |
|---|---|
| Before NaOCl treatment | 10003/(110*100) = 90.9% |
| After NaOCl treatment | 19024/(110*100) = 172.9% |

Figure 34:
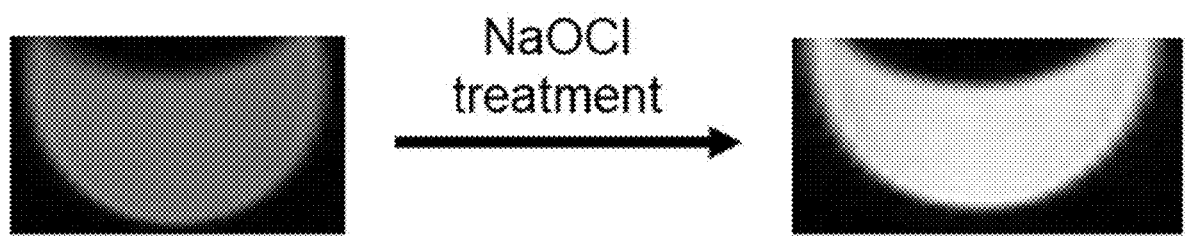
FIG. 34 shows MRI T1 weighted images before and after the treatment of manganese-coordinated bilirubin nanoparticle with reactive oxygen species (hypochlorite).

As shown in Table 1 and FIG. 34, it could be confirmed that the manganese ion-coordinated bilirubin derivative (PEG-BR) nanoparticles of the present invention showed enhanced brightness of the MRI T1 weighted image after the treatment with hypochlorite.

Therefore, it was confirmed from the above results that the bilirubin derivative particles of the present invention can be favorably used as a composition for detection of ROS or an inflammation site accompanied by the ROS.

Although the present invention has been described in detail with reference to the specific features, it will be apparent to those skilled in the art that this description is only for a preferred embodiment and does not limit the scope of the present invention.

What is claimed is:

1. A bilirubin chelate complex comprising:
a plurality of bilirubins each conjugated with a hydrophilic molecule; and
a metal nanoparticle attached by coordinate bonds to at least one of a carboxyl group, a lactam group, or a pyrrole ring of the bilirubin,
wherein the bilirubin chelate complex has a shell-core shape comprising a shell formed by the plurality of bilirubins, and the hydrophilic molecule conjugated with each of the plurality of bilirubins extends from the shell,
wherein the metal nanoparticle comprises a superparamagnetic iron oxide nanoparticle (SPION) or a gold nanoparticle;
the metal nanoparticle is within a core of the shell-core shape; and
the metal nanoparticle within the core is coated with a single layer of the shell formed by the plurality of bilirubins.

2. The bilirubin chelate complex of claim 1, wherein the hydrophilic molecule is selected from the group consisting of dextran, carbodextran, polysaccharide, cyclodextran, pluronic, cellulose, starch, glycogen, carbohydrate, monosaccharide, bisaccharide and oligosaccharide, polyphosphagen, polylactide, poly(lactic-co-glycolic acid), polycaprolactone, polyanhydride, polymaleic acid and polymaleic acid derivatives, poly alkylcyanoacrylate, polyhydroxybutylate, polycarbonate, poly orthoester, polyethyleneglycol, polypropyleneglycol, polyethylenimine, poly-L-lysine, polyglycolide, polymetacrylate, polyvinylpyrrolidone, poly[acrylate], poly[acrylamide], poly[vinylester], poly[vinyl alcohol], polystryene, polyoxide, polyelectrolyte, poly[1-nitropropylene], poly[N-vinyl pyrrolidone], poly[vinyl amine], poly[beta-hydroxyethylmethacrylate], polyethyleneoxide, poly[ethylene oxide-bpropyleneoxide], polylysine, and peptide.

3. The bilirubin chelate complex of claim 1, wherein the hydrophilic molecule is a polyethylene glycol.

4. The bilirubin chelate complex of claim 3, wherein the metal nanoparticle is superparamagnetic iron oxide nanoparticle (SPION).

5. A contrast agent comprising the bilirubin chelate complex of claim 1.

6. A bilirubin chelate complex comprising:
a plurality of bilirubins each conjugated with a hydrophilic molecule; and
a metal nanoparticle attached by coordinate bonds to at least one of a carboxyl group, a lactam group, or a pyrrole ring of the bilirubin,
wherein the bilirubin chelate complex has a shell-core shape comprising a shell formed by the plurality of bilirubins, and the hydrophilic molecule conjugated with each of the plurality of bilirubins extends from the shell,
wherein the metal nanoparticle comprises a superparamagnetic iron oxide nanoparticle (SPION) or a gold nanoparticle; and
wherein the metal nanoparticle is enclosed within the core, and the metal nanoparticle enclosed within the core is in the form of a single metal particle.

7. A bilirubin chelate complex comprising:
a plurality of bilirubins each conjugated with a hydrophilic molecule; and
a metal nanoparticle attached by coordinate bonds to at least one of a carboxyl group, a lactam group, or a pyrrole ring of the bilirubin,
wherein the bilirubin chelate complex has a shell-core shape comprising a shell formed by the plurality of bilirubins, and the hydrophilic molecule conjugated with each of the plurality of bilirubins extends from the shell,
wherein the metal nanoparticle comprises a superparamagnetic iron oxide nanoparticle (SPION) or a gold nanoparticle; and
wherein the metal nanoparticle is enclosed within the core, and the metal nanoparticle enclosed within the core is in the form of clustered metal particles.

8. The bilirubin chelate complex of claim 6, wherein the hydrophilic molecule is selected from the group consisting of dextran, carbodextran, polysaccharide, cyclodextran, pluronic, cellulose, starch, glycogen, carbohydrate, monosaccharide, bisaccharide and oligosaccharide, polyphosphagen, polylactide, poly(lactic-co-glycolic acid), polycaprolactone, polyanhydride, polymaleic acid and polymaleic acid derivatives, polyalkylcyanoacrylate, polyhydroxybutylate, polycarbonate, polyorthoester, polyethyleneglycol, polypropyleneglycol, polyethylenimine, poly-L-lysine, polyglycolide, polymetacrylate, polyvinylpyrrolidone, poly[acrylate], poly[acrylamide], poly[vinylester], poly[vinyl alcohol], polystryene, polyoxide, polyelectrolyte, poly[1-nitropropylene], poly[N-vinyl pyrrolidone], poly[vinyl amine], poly[beta-hydroxyethylmethacrylate], polyethyleneoxide, poly[ethylene oxide-bpropyleneoxide], polylysine, and peptide.

9. The bilirubin chelate complex of claim 6, wherein the hydrophilic molecule is a polyethylene glycol.

10. The bilirubin chelate complex of claim 9, wherein the metal nanoparticle is superparamagnetic iron oxide nanoparticle (SPION).

11. A contrast agent comprising the bilirubin chelate complex of claim 7.

\* \* \* \* \*